(12) United States Patent
Ashrafi et al.

(10) Patent No.: US 9,267,877 B2
(45) Date of Patent: Feb. 23, 2016

(54) SYSTEM AND METHOD FOR MAKING CONCENTRATION MEASUREMENTS WITHIN A SAMPLE MATERIAL USING ORBITAL ANGULAR MOMENTUM

(71) Applicants: Solyman Ashrafi, Plano, TX (US); Roger Linquist, Dallas, TX (US); Nima Ashrafi, Plano, TX (US)

(72) Inventors: Solyman Ashrafi, Plano, TX (US); Roger Linquist, Dallas, TX (US); Nima Ashrafi, Plano, TX (US)

(73) Assignee: NxGen Partners IP, LLC, Dallas, TX (US)

( * ) Notice: Subject to any disclaimer, the term of this patent is extended or adjusted under 35 U.S.C. 154(b) by 0 days.

(21) Appl. No.: 14/339,836

(22) Filed: Jul. 24, 2014

(65) Prior Publication Data
US 2015/0260650 A1 Sep. 17, 2015

Related U.S. Application Data

(60) Provisional application No. 61/951,834, filed on Mar. 12, 2014.

(51) Int. Cl.
*G01N 21/17* (2006.01)
*G01N 21/59* (2006.01)
*G01N 24/00* (2006.01)

(52) U.S. Cl.
CPC ............... *G01N 21/17* (2013.01); *G01N 21/59* (2013.01); *G01N 24/00* (2013.01)

(58) Field of Classification Search
None
See application file for complete search history.

(56) References Cited

U.S. PATENT DOCUMENTS

| | | |
|---|---|---|
| 3,459,466 A | 8/1969 | Giordmaine |
| 3,614,722 A | 10/1971 | Jones |
| 4,379,409 A | 4/1983 | Primbsch et al. |
| 4,503,336 A | 3/1985 | Hutchin et al. |
| 4,736,463 A | 4/1988 | Chavez |
| 4,862,115 A | 8/1989 | Lee et al. |
| 5,051,754 A | 9/1991 | Newberg |
| 5,220,163 A | 6/1993 | Toughlian et al. |
| 5,222,071 A | 6/1993 | Pezeshki et al. |
| 5,272,484 A | 12/1993 | Labaar |
| 5,543,805 A | 8/1996 | Thaniyavarn |
| 5,555,530 A | 9/1996 | Meehan |
| 6,337,659 B1 | 1/2002 | Kim |
| 6,992,829 B1 | 1/2006 | Jennings et al. |

(Continued)

FOREIGN PATENT DOCUMENTS

WO WO 2011028109 A1 * 3/2011
WO WO 2012172471 A2 * 12/2012

(Continued)

OTHER PUBLICATIONS

Darla et al., "Optical twisters: beams having twists in both phase and amplitude," 2010, Complex Light and Optical Forces IV, edited by Galvez et al., Proc. of SPIE vol. 7613, pp. 761304-1 to 761304-8.*

(Continued)

*Primary Examiner* — Gordon J Stock, Jr.
(74) *Attorney, Agent, or Firm* — Howison & Arnott, LLP

(57) ABSTRACT

Signal generation circuitry generates a first signal having at least one orbital angular momentum applied thereto and applies the first signal to the sample. A detector for receives the first signal after it passes through the sample and determines the concentration of the material within the sample based on a detected value of orbital angular momentum with the first signal received from the sample.

30 Claims, 21 Drawing Sheets

(56) References Cited

U.S. PATENT DOCUMENTS

| | | | |
|---|---|---|---|
| 7,577,165 | B1 | 8/2009 | Barrett |
| 7,729,572 | B1 | 6/2010 | Pepper et al. |
| 7,792,431 | B2 | 9/2010 | Jennings et al. |
| 8,432,884 | B1 | 4/2013 | Ashrafi |
| 8,503,546 | B1 | 8/2013 | Ashrafi |
| 8,559,823 | B2 | 10/2013 | Izadpanah et al. |
| 8,811,366 | B2 | 8/2014 | Ashrafi |
| 9,077,577 | B1 | 7/2015 | Ashrafi |
| 2002/0164806 | A1 | 11/2002 | Collins |
| 2004/0196465 | A1* | 10/2004 | Arnold et al. ............ 356/432 |
| 2005/0254826 | A1 | 11/2005 | Jennings et al. |
| 2005/0259914 | A1 | 11/2005 | Padgett et al. |
| 2006/0126183 | A1* | 6/2006 | Hasman .................. 359/573 |
| 2008/0037004 | A1 | 2/2008 | Shamir et al. |
| 2010/0013696 | A1 | 1/2010 | Schmitt et al. |
| 2010/0317959 | A1* | 12/2010 | Elgort et al. ............. 600/410 |
| 2010/0327866 | A1 | 12/2010 | Albu et al. |
| 2012/0207470 | A1 | 8/2012 | Djordjevic et al. |
| 2013/0027774 | A1 | 1/2013 | Bovino et al. |
| 2014/0353475 | A1* | 12/2014 | Meyers et al. .......... 250/216 |
| 2014/0355624 | A1 | 12/2014 | Li et al. |
| 2015/0098697 | A1 | 4/2015 | Marom et al. |

FOREIGN PATENT DOCUMENTS

| | | | |
|---|---|---|---|
| WO | WO 2013179023 | A1 * | 12/2013 |
| WO | WO 2013186648 | A2 * | 12/2013 |

OTHER PUBLICATIONS

Zhang et al., "High-dimensional orbital angular momentum entanglement concentration based on Laguerre-Gaussian mode selection," 2013, Laser Physics Letters, 10, 5 pages.*

PCT: International Search Report and Written Opinion of PCT/US2015/019177 (related application), Jun. 25, 2015, 8 pgs.

Solyman Ashrafi, Channeling Radiation of Electrons in Crystal Lattices, Essays on Classical and Quantum Dynamics, Gordon and Breach Science Publishers, 1991.

Solyman Ashrafi, Solar Flux Forecasting Using Mutual Information with an Optimal Delay, Advances in the Astronautical Sciences, American Astronautical Society, vol. 84 Part II, 1993.

Solyman Ashrafi, PCS system design issues in the presence of microwave OFS, Electromagnetic Wave Interactions, Series on Stability, Vibration and Control of Systems, World Scientific, Jan. 1996.

Solyman Ashrafi, Performance Metrics and Design Parameters for an FSO Communications Link Based on Multiplexing of Multiple Orbital-Angular-Momentum Beams, Globecom2014 OWC Workshop, 2014.

Solyman Ashrafi, Optical Communications Using Orbital Angular Momentum Beams, Adv. Opt. Photon. 7, 66-106, Advances in Optics and Photonic, 2015.

Solyman Ashrafi, Performance Enhancement of an Orbital-Angular-Momentum-Based Free-Space Optical Communication Link through Beam Divergence Controlling, OSA Technical Digest (online), paper M2F.6. The Optical Society, 2015.

Solyman Ashrafi, Experimental demonstration of enhanced spectral efficiency of 1.18 symbols/s/Hz using multiple-layer-overlay modulation for QPSK over a 14-km fiber link. OSA Technical Digest (online), paper JTh2A.63. The Optical Society, 2014.

Solyman Ashrafi, Link Analysis of Using Hermite-Gaussian Modes for Transmitting Multiple Channels in a Free-Space Optical Communication System, The Optical Society, vol. 2, No. 4, Apr. 2015.

Solyman Ashrafi, Performance Metrics and Design Considerations for a Free-Space Optical Orbital-Angular-Momentum-Multiplexed Communication Link, The Optical Society, vol. 2, No. 4, Apr. 2015.

Solyman Ashrafi, Demonstration of Distance Emulation for an Orbital-Angular-Momentum Beam. OSA Technical Digest (online), paper STh1F.6. The Optical Society, 2015.

Solyman Ashrafi, Free-Space Optical Communications Using Orbital-Angular-Momentum Multiplexing Combined with MIMO-Based Spatial Multiplexing. Optics Letters, vol. 40, No. 18, Sep. 4, 2015.

Solyman Ashrafi, Enhanced Spectral Efficiency of 2.36 bits/s/Hz Using Multiple Layer Overlay Modulation for QPSK over a 14-km Single Mode Fiber Link. OSA Technical Digest (online), paper SW1M.6. The Optical Society, 2015.

Solyman Ashrafi, Experimental Demonstration of a 400-Gbit/s Free Space Optical Link Using Multiple Orbital-Angular-Momentum Beams with Higher Order Radial Indices. OSA Technical Digest (online), paper SW4M.5. The Optical Society, 2015.

Solyman Ashrafi, Experimental Demonstration of 16-Gbit/s Millimeter-Wave Communications Link using Thin Metamaterial Plates to Generate Data-Carrying Orbital-Angular-Momentum Beams, ICC 2015, London, UK, 2014.

Solyman Ashrafi, Experimental Demonstration of Using Multi-Layer-Overlay Technique for Increasing Spectral Efficiency to 1.18 bits/s/Hz in a 3 Gbit/s Signal over 4-km Multimode Fiber. OSA Technical Digest (online), paper JTh2A.63. The Optical Society, 2015.

Solyman Ashrafi, Experimental Measurements of Multipath-Induced Intra- and Inter-Channel Crosstalk Effects in a Millimeter-Wave Communications Link using Orbital-Angular-Momentum Multiplexing, ICC 2015, London, UK, 2014.

Solyman Ashrafi, Performance Metrics for a Free-Space Communication Link Based on Multiplexing of Multiple Orbital Angular Momentum Beams with Higher Order Radial Indice. OSA Technical Digest (online), paper JTh2A.62. The Optical Society, 2015.

Solyman Ashrafi, 400-Gbit/s Free-Space Optical Communications Link Over 120-meter Using Multiplexing of 4 Collocated Orbital-Angular-Momentum Beams. OSA Technical Digest (online), paper M2F.1. The Optical Society, 2015.

Solyman Ashrafi, Experimental Demonstration of Two-Mode 16-Gbit/s Free-Space mm-Wave Communications Link Using Thin Metamaterial Plates to Generate Orbital Angular Momentum Beams, Optica, vol. 1, No. 6, Dec. 2014.

Solyman Ashrafi, Demonstration of an Obstruction-Tolerant Millimeter-Wave Free-Space Communications Link of Two 1-Gbaud 16-QAM Channels using Bessel Beams Containing Orbital Angular Momentum, Third International Conference on Optical Angular Momentum (ICOAM), Aug. 4-7, 2015, New York USA.

Wang et al: "Terabit free-space data transmission employing orbital angular momentum multiplexing", Nature Photonics, vol. 6, Jul. 2012, pp. 488-496.

Solyman Ashrafi, An Information Theoretic Framework to Increase Spectral Efficiency, IEEE Transaction on Information Theory, vol. XX, No. Y, Oct. 2014, Dallas, Texas.

H. Yao et al, Patch Antenna Array for the Generation of Millimeter-wave Hermite-Gaussian Beams, IEEE Antennas and Wireless Propagation Letters, (pending publication).

Yongxiong Ren et al, Experimental Investigation of Data Transmission Over a Graded-index Multimode Fiber Using the Basis of Orbital Angular Momentum Modes (pending publication).

M. Nouri et al., Perturbations of Laguerre-Gaussian Beams by Chiral Molecules (pending publication).

Solyman Ashrafi, Acoustically induced stresses in elastic cylinders and their visualization, The Journal of the Acoustical Society of America 82(4):1378-1385, Sep. 1987.

Solyman Ashrafi, Splitting of channeling-radiation peaks in strained-layer superlattices, Journal of the Optical Society of America B 8(12), Nov. 1991.

* cited by examiner

SYSTEM AND METHOD FOR MAKING CONCENTRATION MEASUREMENTS WITHIN A SAMPLE MATERIAL USING ORBITAL ANGULAR MOMENTUM

CROSS-REFERENCE TO RELATED APPLICATIONS

This application claims benefit of U.S. Provisional Application No. 61/951,834, filed Mar. 12, 2014, entitled CONCENTRATION MEASUREMENTS USING PHOTON ORBITAL ANGULAR MOMENTUM, the specification of which is incorporated by reference herein in its entirety.

TECHNICAL FIELD

The present invention relates to concentration measurements of various organic and non-organic materials, and more particularly, to concentration measurements of organic and non-organic materials using the orbital angular momentum of waves passed through a sample of the material.

BACKGROUND

Concentration measurements of organic and non-organic materials within human tissue is an increasingly important aspect of healthcare for individuals. The development of non-invasive measurement techniques for monitoring biological and metabolic agents within human tissue is an important aspect of diagnosis therapy of various human diseases and may play a key role in the proper management of diseases. One example of a biological agent that may be monitored for within human tissue is glucose. Glucose ($C_6H_{12}O_6$) is a monosaccharide sugar and is one of the most important carbohydrate nutrient sources. Glucose is fundamental to almost all biological processes and is required for the production of ATP adenosine triphosphate and other essential cellular components. The normal range of glucose concentration within human blood is 70-160 mg/dl depending on the time of the last meal, the extent of physical tolerance and other factors. Freely circulating glucose molecules stimulate the release of insulin from the pancreas. Insulin helps glucose molecules to penetrate the cell wall by binding two specific receptors within cell membranes which are normally impermeable to glucose.

One disease associated with issues related to glucose concentrations is diabetes. Diabetes is a disorder caused by the decreased production of insulin, or by a decreased ability to utilize insulin and transport the glucose across cell membranes. As a result, a high potentially dangerous concentration of glucose can accumulate within the blood (hyperglycemia) during the disease. Therefore, it is of great importance to maintain blood glucose concentration within a normal range in order to prevent possible severe physiological complications.

One significant role of physiological glucose monitoring is the diagnosis and management of several metabolic diseases, such as diabetes mellitus (or simply diabetes). There are a number of invasive and non-invasive techniques presently used for glucose monitoring. The problem with existing non-invasive glucose monitoring techniques is that a clinically acceptable process has not yet been determined. Standard techniques from the analysis of blood currently involve an individual puncturing a finger and subsequent analysis of collected blood samples from the finger. In recent decades, non-invasive blood glucose monitoring has become an increasingly important topic of investigation in the realm of biomedical engineering. In particular, the introduction of optical approaches have caused some advances within the field. Advances in optics have led to a focused interest in optical imaging technologies and the development of non-invasive imaging systems. The application of optical methods to monitoring in cancer diagnostics and treatment is also a growing field due to the simplicity and low risk of optical detection methods.

Many optical techniques for sensing different tissue metabolites and glucose in living tissue have been in development over the last 50 years. These methods have been based upon florescent, near infrared and mid-infrared spectroscopy, Raman spectroscopy, photoacoustics, optical coherence tomography and other techniques. However, none of these techniques that have been tried have proved completely satisfactory.

Another organic component lending itself to optical material concentration sensing involves is human skin. The defense mechanisms of human skin are based on the action of antioxidant substances such as carotenoids, vitamins and enzymes. Beta carotene and lycopene represent more than 70% of the carotenoids in the human organism. The topical or systematic application of beta carotene and lycopene is a general strategy for improving the defense system of the human body. The evaluation and optimization of this treatment requires the measurement of the b-carotene and lycopene concentrations in human tissue, especially in the human skin as the barrier to the environment.

Thus, an improved non-invasive technique enabling the detection of concentrations of various materials within a human body or other types of samples would have a number of applications within the medical field.

SUMMARY

The present invention, as disclosed and describe herein, in one aspect thereof, comprises an apparatus for measuring the concentration of a material within a sample. Signal generation circuitry generates a first signal having at least one orbital angular momentum applied thereto and applies the first signal to the sample. A detector for receives the first signal after it passes through the sample and determines the concentration of the material within the sample based on a detected value of orbital angular momentum with the first signal received from the sample.

BRIEF DESCRIPTION OF THE DRAWINGS

For a more complete understanding, reference is now made to the following description taken in conjunction with the accompanying Drawings in which.

DETAILED DESCRIPTION

Figure 1:
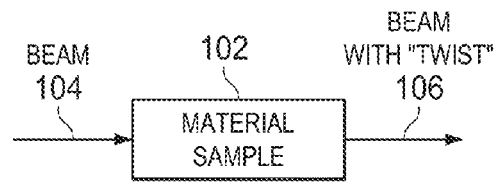
FIG. 1 illustrates a general representation of a manner for determining a concentration of a particular material within a sample using a light beam or other wave.

Referring now to the drawings, wherein like reference numbers are used herein to designate like elements throughout, the various views and embodiments of system and method for making concentration measurements within a sample material using orbital angular momentum are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to the drawings, and more particularly to FIG. 1, there is illustrated a general representation of the manner in which the concentration of a particular material sample 102 may be monitored using orbital angular momentum applied to a light beam or other wave transmitted through the material sample 102. The material sample 102 has a beam 104 shined through the length of the material sample 102. After passing through the material sample 102, the exiting beam 106 leaves the material sample and may be analyzed to determine various concentration characteristics within the material sample 102. The manner in which the different characteristics of the material sample 102 may be determined within the exiting beam 106 is achieved with respect to an analysis of the orbital angular momentum signatures that are imparted to the exiting beam 106 by the concentrations within the material sample 102.

Figure 2:
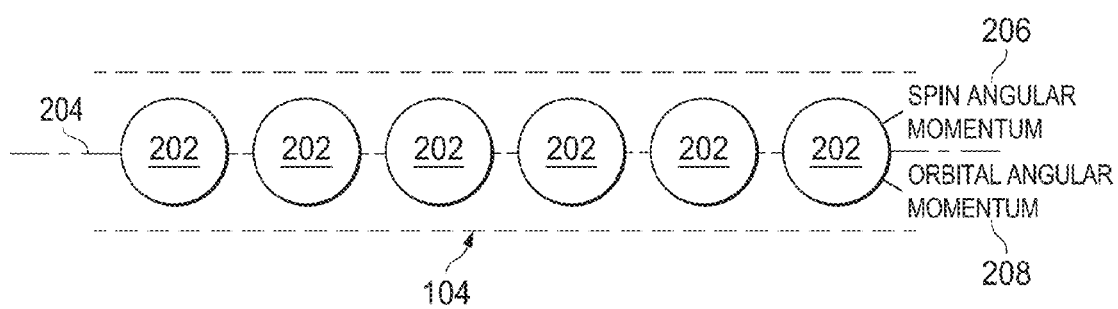
FIG. 2 illustrates a light beam having orbital angular momentum imparted thereto.

Referring now also to FIG. 2, there is illustrated one embodiment of a beam for use with the system. A light beam 104 consists of a stream of photons 202 within the light beam 104. Each photon has an energy $\pm\hbar\omega$ and a linear momentum of $\pm\hbar k$ which is directed along the light beam axis 204 perpendicular to the wavefront. Independent of the frequency, each photon 202 within the light beam has a spin angular momentum 206 of $\pm\hbar$ aligned parallel or antiparallel to the direction of light beam propagation. Alignment of all of the photons 202 spins gives rise to a circularly polarized light beam. In addition to the circular polarization, the light beams also may carry an orbital angular momentum 208 which does not depend on the circular polarization and thus is not related to photon spin.

Figure 3:
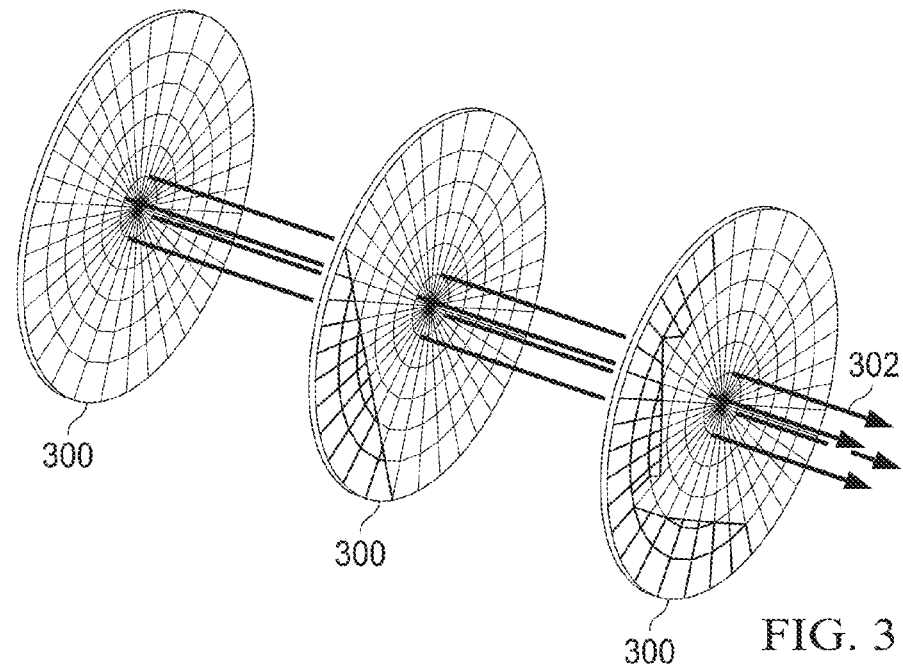
FIG. 3 illustrates a series of parallel wavefronts.

Lasers are widely used in optical experiments as the source of well-behaved light beams of a defined frequency. A laser may be used for providing the light beam 104 as described with respect to FIG. 1. The energy flux in any light beam 104 is given by the Poynting vector which may be calculated from the vector product of the electric and magnetic fields within the light beam. In a vacuum or any isotropic material, the Poynting vector is parallel to the wave vector and perpendicular to the wavefront of the light beam. In a normal laser light, the wavefronts 300 are parallel as illustrated in FIG. 3. The wave vector and linear momentum of the photons are directed along the axis in a z direction 302. The field distributions of such light beams are paraxial solutions to Maxwell's wave equation but although these simple beams are the most common, other possibilities exist.

Figure 4:
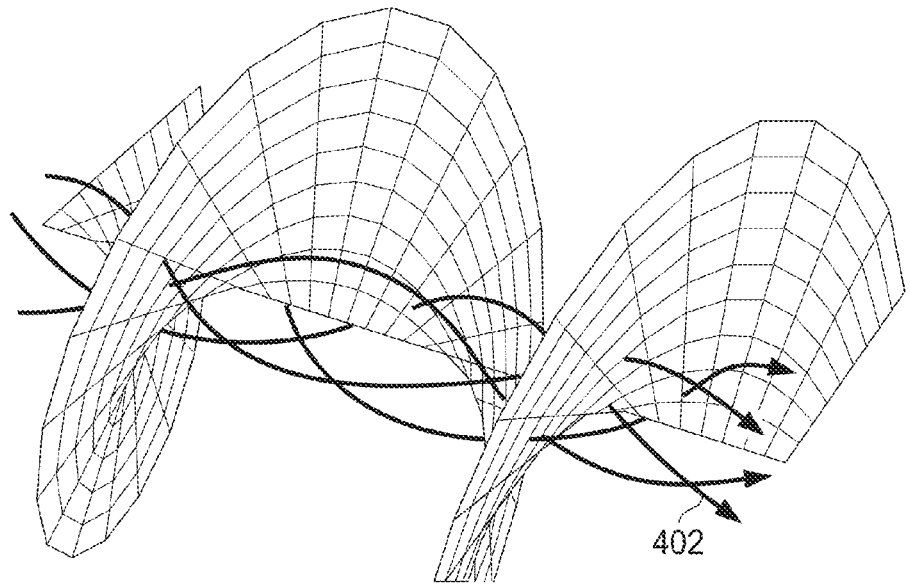
FIG. 4 illustrates a wavefront having a Poynting vector spiraling around a direction of propagation of the wavefront.

For example, beams that have l intertwined helical fronts are also solutions of the wave equation. The structure of these complicated beams is difficult to visualize, but their form is familiar from the l=3 fusilli pasta. Most importantly, the wavefront has a Poynting vector and a wave vector that spirals around the light beam axis direction of propagation as illustrated in FIG. 4 at 402.

A Poynting vector has an azimuthal component on the wave front and a non-zero resultant when integrated over the beam cross-section. The spin angular momentum of circularly polarized light may be interpreted in a similar way. A beam with a circularly polarized planer wave front, even though it has no orbital angular momentum, has an azimuthal component of the Poynting vector proportional to the radial intensity gradient. This integrates over the cross-section of the light beam to a finite value. When the beam is linearly polarized, there is no azimuthal component to the Poynting vector and thus no spin angular momentum.

Thus, the momentum of each photon 202 within the light beam 104 has an azimuthal component. A detailed calculation of the momentum involves all of the electric fields and magnetic fields within the light beam, particularly those electric and magnetic fields in the direction of propagation of the beam. For points within the beam, the ratio between the azimuthal components and the z components of the momentum is found to be l/kr. The linear momentum of each photon 202 within the light beam 104 is given by $\hbar$ k, so if we take the cross product of the azimuthal component within a radius vector, r, we obtain an orbital momentum for a photon 202 of $1\hbar$. Note also that the azimuthal component of the wave vectors is 1/r and independent of the wavelength.

Figure 5:
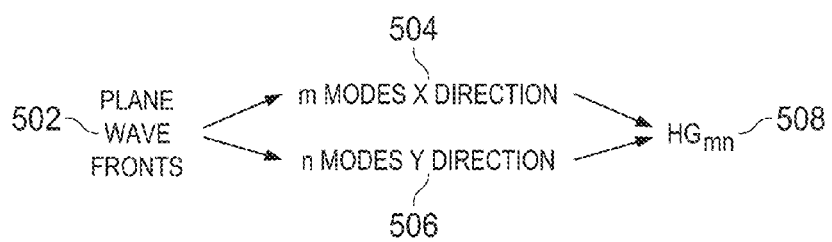
FIG. 5 illustrates a plane wavefront while FIG. 6 helical wavefront.
Figure 6:
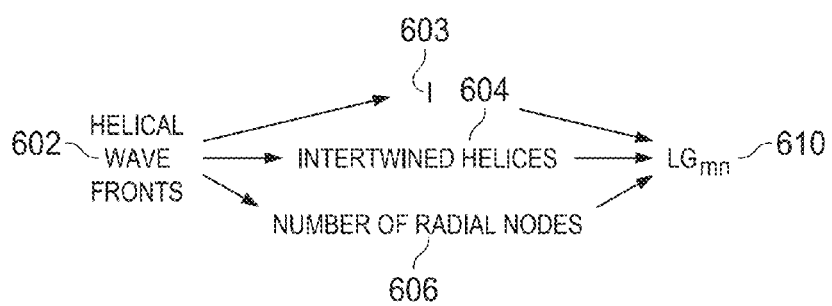

Referring now to FIGS. 5 and 6, there are illustrated plane wavefronts and helical wavefronts. Ordinarily, laser beams with plane wavefronts 502 are characterized in terms of Hermite-Gaussian modes. These modes have a rectangular symmetry and are described by two mode indices m 504 and n 506. There are m nodes in the x direction and n nodes in the y direction. Together, the combined modes in the x and y direction are labeled $HG_{mn}$ 508. In contrast, as shown in FIG. 6 beams with helical wavefronts 602 are best characterized in terms of Laguerre-Gaussian modes which are described by indices l 603, the number of intertwined helices 604, and p, the number of radial nodes 606. The Laguerre-Gaussian modes are labeled $LG_{mn}$ 610. For l≠0, the phase singularity on a light beam 104 results in 0 on axis intensity. When a light beam 104 with a helical wavefront is also circularly polarized, the angular momentum has orbital and spin components, and the total angular momentum of the light beam is $(l\pm\hbar)$ per photon.

Using the orbital angular momentum state of the transmitted energy signals, physical information can be embedded within the electromagnetic radiation transmitted by the signals. The Maxwell-Heaviside equations can be represented as:

$$\nabla \cdot E = \frac{\rho}{\varepsilon_0}$$

$$\nabla \times E = -\frac{\partial B}{\partial t}$$

$$\nabla \cdot B = 0$$

$$\nabla \times B = \varepsilon_0 \mu_0 \frac{\partial E}{\partial t} + \mu_0 j(t, x) \text{the}$$

where $\nabla$ is the del operator, E is the electric field intensity and B is the magnetic flux density. Using these equations, we can derive 23 symmetries/conserve quantities from Maxwell's original equations. However, there are only ten well-known conserve quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3 x (|E|^2 + c^2|B|^2)$$

$$\frac{dU^{mech}}{dt} + \frac{dU^{em}}{dt} + \oint_{S'} d^2 x' \hat{n}' \cdot S = 0$$

The space symmetry, i.e., the conservation of system linear momentum representing the electromagnetic Doppler shift can be represented by the equations:

$$P = \sum_i m_i \gamma_i v_i + \varepsilon_0 \int d^3 x (E \times B)$$

$$\frac{dp^{mech}}{dt} + \frac{dp^{em}}{dt} + \oint_{S'} d^2 x' \hat{n}' \cdot T = 0$$

The conservation of system center of energy is represented by the equation:

$$R = \frac{1}{H} \sum_i (x_i - x_0) m_i \gamma_i c^2 + \frac{\varepsilon_0}{2H} \int d^3 x (x - x_0)(|E|^2 + c^2|B|^2)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{S'} d^2 x' \hat{n}' \cdot M = 0$$

For radiation beams in free space, the EM field angular momentum $J^{em}$ can be separated into two parts:

$$J^{em} = \varepsilon_0 \int_V d^3 x' (E \times A) + \varepsilon_0 \int_V d^3 x' E_i [(x' - x_0) \times \nabla] A_i$$

For each singular Fourier mode in real valued representation:

$$J^{em} = -i \frac{\varepsilon_0}{2\omega} \int_{V'} d^3 x' (E^* \times E) - i \frac{\varepsilon_0}{2\omega} \int_{V'} d^3 x' E_i' [(x' - x_0) \times \nabla] E_i$$

The first part is the EM spin angular momentum $S^{em}$, its classical manifestation is wave polarization. And the second part is the EM orbital angular momentum $L^{em}$ its classical manifestation is wave helicity. In general, both EM linear momentum $P^{em}$, and EM angular momentum $J^{em} = L^{em} + S^{em}$ are radiated all the way to the far field.

By using Poynting theorem, the optical vorticity of the signals may be determined according to the optical velocity equation:

$$\frac{\partial U}{\partial t} + \nabla \cdot S = 0,$$

where S is the Poynting vector $$S = \tfrac{1}{4}(E \times H^* + E^* \times H),$$

and U is the energy density $$U = \tfrac{1}{4}(\varepsilon|E|^2 + \mu_0|H|^2),$$

with E and H comprising the electric field and the magnetic field, respectively, and $\epsilon$ and $\mu_0$ being the permittivity and the permeability of the medium, respectively. The optical vorticity V may then be determined by the curl of the optical velocity according to the equation:

$$V = \nabla \times v_{opt} = \nabla \times \left( \frac{E \times H^* + E^* \times H}{\epsilon |E|^2 + \mu_0 |H|^2} \right)$$

Figure 7:
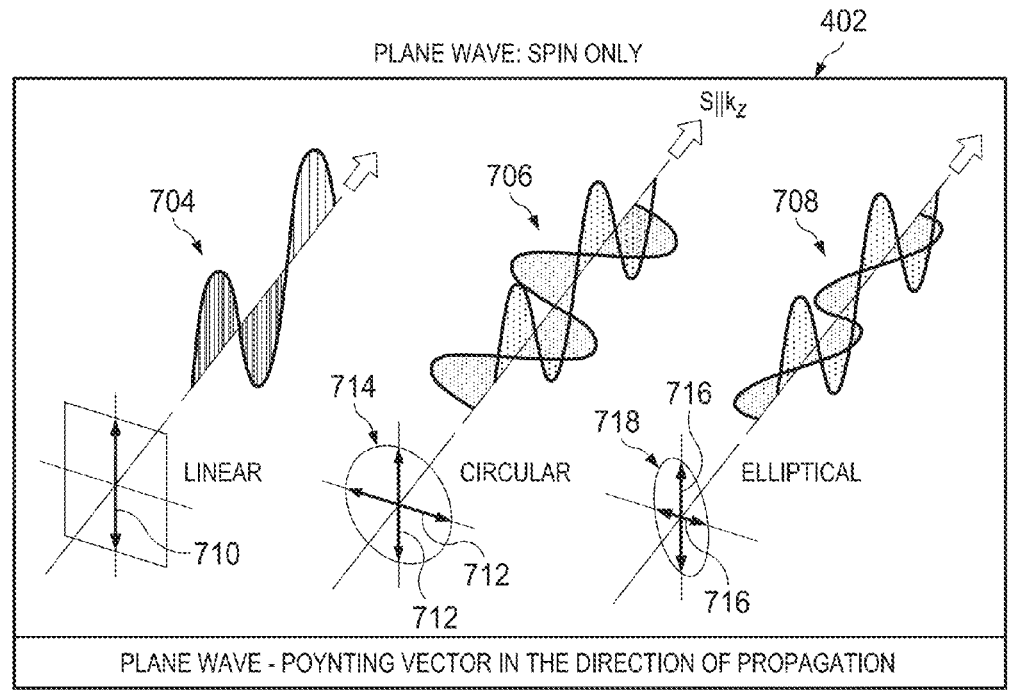
FIG. 7 illustrates a plane wave having only variations in the spin vector.
Figure 8:
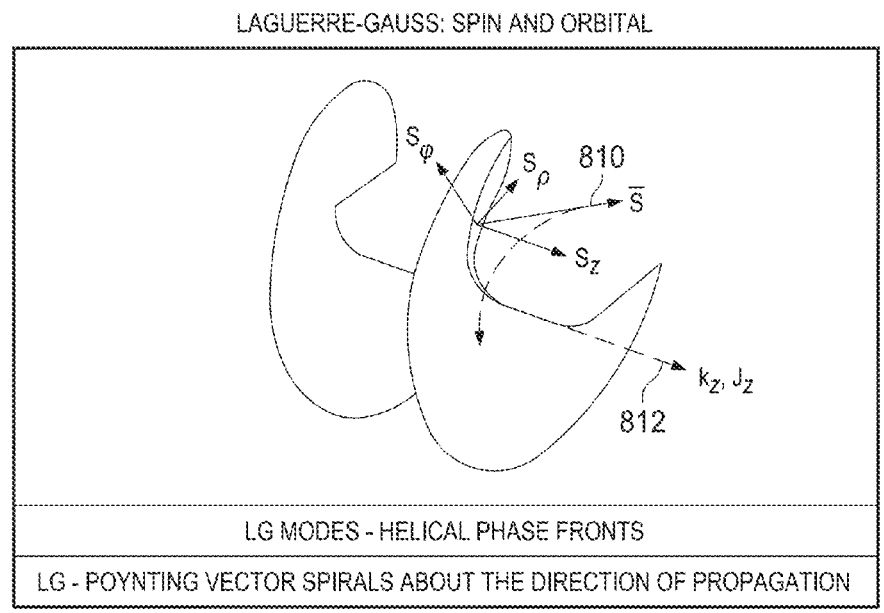
FIG. 8 illustrates the application of a unique orbital angular momentum to a wave.

Referring now to FIGS. 7 and 8, there are illustrated the manner in which a signal and an associated Poynting vector of the signal vary in a plane wave situation (FIG. 7) where only the spin vector is altered, and in a situation wherein the spin and orbital vectors are altered in a manner to cause the Poynting vector to spiral about the direction of propagation (FIG. 8).

In the plane wave situation, illustrated in FIG. 7, when only the spin vector of the plane wave is altered, the transmitted signal may take on one of three configurations. When the spin vectors are in the same direction, a linear signal is provided as illustrated generally at 704. It should be noted that while 704 illustrates the spin vectors being altered only in the x direction to provide a linear signal, the spin vectors can also be altered in the y direction to provide a linear signal that appears similar to that illustrated at 704 but in a perpendicular orientation to the signal illustrated at 704. In linear polarization such as that illustrated at 710, the vectors for the signal are in the same direction and have a same magnitude.

Within a circular polarization as illustrated at 706, the signal vectors 712 are 90 degrees to each other but have the same magnitude. This causes the signal to propagate as illustrated at 706 and provide the circular polarization 714 illustrated in FIG. 7. Within an elliptical polarization 708, the signal vectors 716 are also 90 degrees to each other but have differing magnitudes. This provides the elliptical polarizations 718 illustrated for the signal propagation 708. For the plane waves illustrated in FIG. 7A, the Poynting vector is maintained in a constant direction for the various signal configurations illustrated therein.

The situation in FIG. 8 illustrates when a unique orbital angular momentum is applied to a signal. When this occurs, Poynting vector S 810 will spiral around the general direction of propagation 812 of the signal. The Poynting vector 810 has three axial components $S_\phi$, $S_p$ and $S_z$ which vary causing the vector to spiral about the direction of propagation 612 of the signal. The changing values of the various vectors comprising the Poynting vector 810 may cause the spiral of the Poynting vector to be varied in order to enable signals to be transmitted on a same wavelength or frequency as will be more fully described herein. Additionally, the values of the orbital angular momentum indicated by the Poynting vector 410 may be measured to determine concentrations associated with particular materials being processed by a concentration scanning mechanism.

Figure 9A:
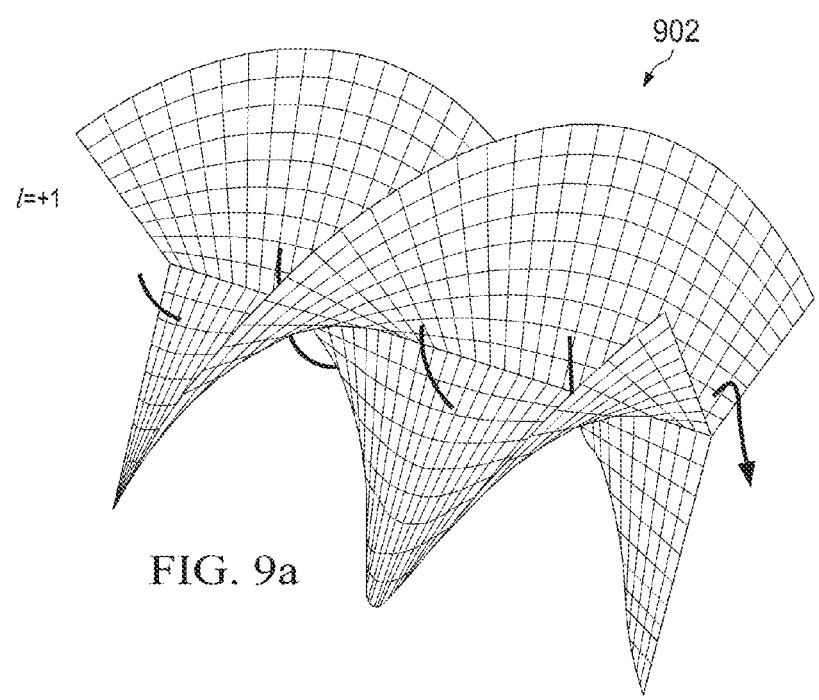
FIGS. 9a-9c illustrate the differences between signals having different orbital angular momentum applied thereto.
Figure 9B:
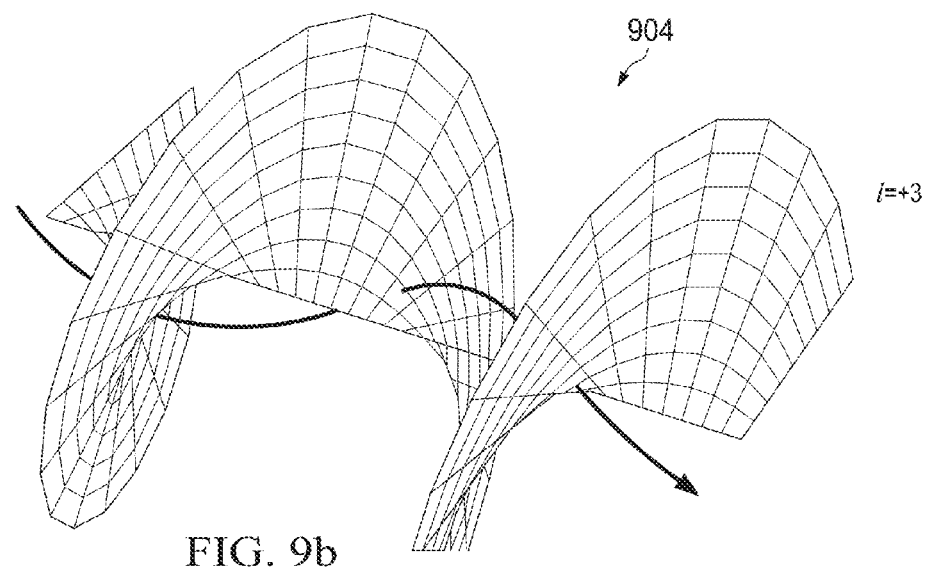
Figure 9C:
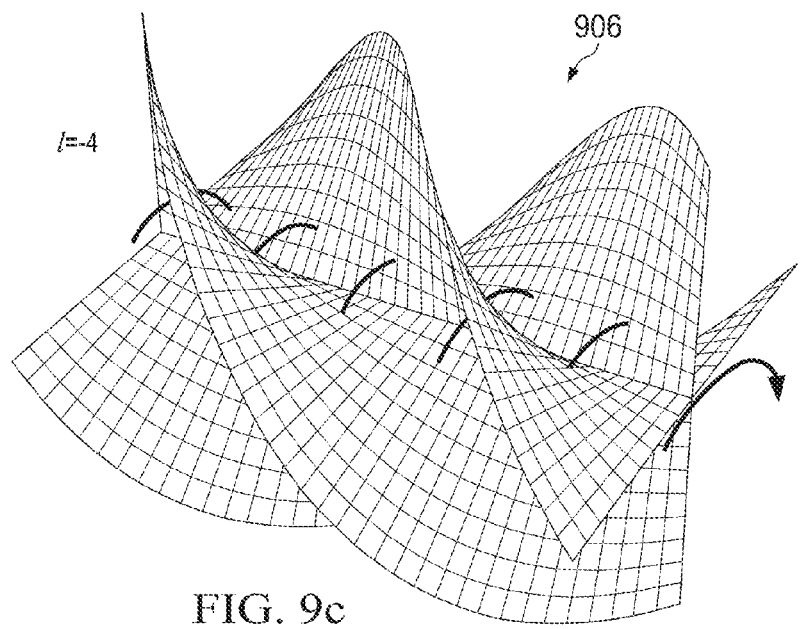

FIGS. 9a-9c illustrate the differences in signals having a different helicity (i.e., orbital angular momentum applied thereto). The differing helicities would be indicative of differing concentration of materials within a sample that a beam was being passed through. By determining the particular orbital angular momentum signature associated with a signal, the concentration amounts of the material could be determined. Each of the spiraling Poynting vectors associated with a signal 902, 904 and 906 provides a different-shaped signal. Signal 902 has an orbital angular momentum of +1, signal 904 has an orbital angular momentum of +3 and signal 906 has an orbital angular momentum of −4. Each signal has a distinct orbital angular momentum and associated Poynting vector enabling the signal to be indicative of a particular concentration of material that is associated with the detected orbital angular momentum. This allows determinations of concentrations of various types of materials to be determined from a signal since the orbital angular momentums are separately detectable and provide a unique indication of the concentration of the particular material that has affected the orbital angular momentum of the signal transmitted through the sample material.

Figure 10:
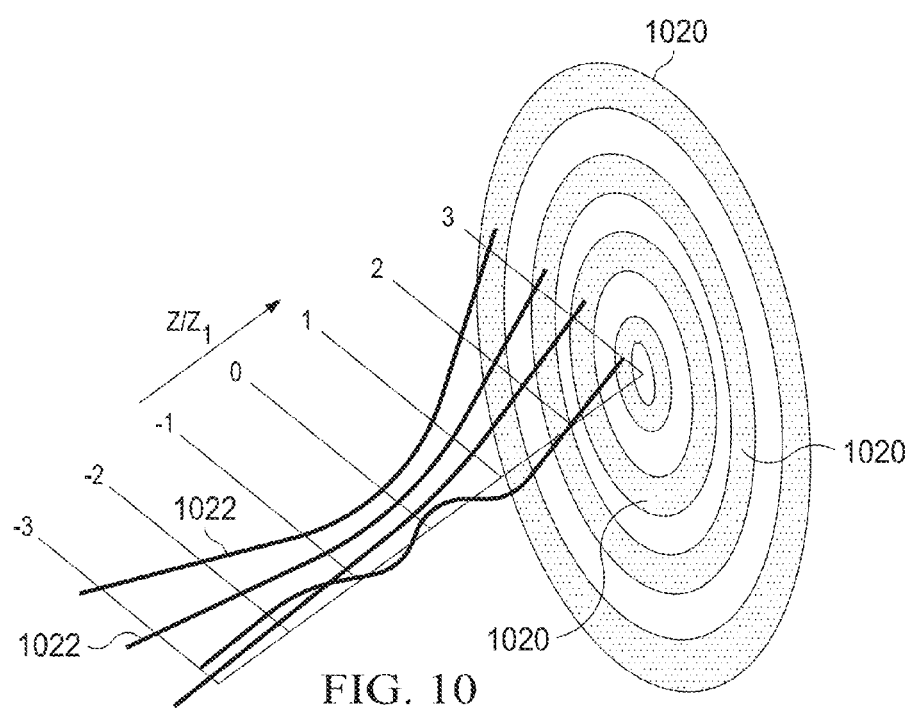
FIG. 10 illustrates the propagation of Poynting vectors for various eigenmodes.

FIG. 10 illustrates the propagation of Poynting vectors for various Eigen modes. Each of the rings 1020 represents a different Eigen mode or twist representing a different orbital angular momentum. Each of the different orbital angular momentums is associated with a particular concentration of a particular material. Detection of orbital angular momentums provide an indication of the associated material concentration that is being monitored by the apparatus. Each of the rings 1020 represents a different concentration of a selected material that is being monitored. Each of the Eigen modes has a Poynting vector 1022 for generating the rings indicating different material concentrations.

Figure 11:
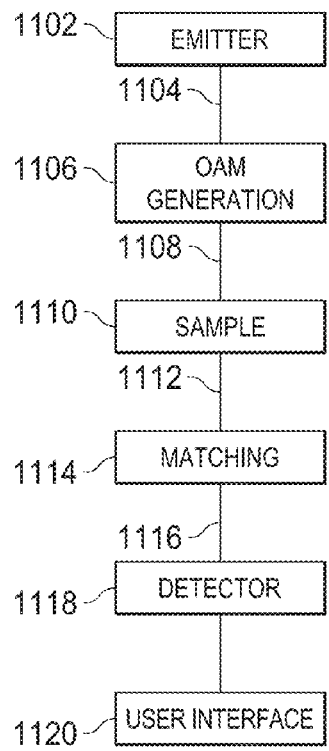
FIG. 11 illustrates a block diagram of an apparatus for providing concentration measurements of various materials using orbital angular momentum.

Referring now to FIG. 11, there is illustrated a block diagram of the apparatus for providing concentration measurements of various materials responsive to the orbital angular momentum detected by the apparatus in accordance with the principles described herein above. An emitter 1102 transmits wave energy 1104 that comprises a series of plane waves. The emitter 1102 may provide a series of plane waves such as those describes previously with respect to FIG. 3. The orbital angular momentum generation circuitry 1106 generates a series of waves having an orbital angular momentum applied to the waves 1108 in a known manner. The orbital angular momentum generation circuitry 1106 may utilize holograms or some other type of orbital angular momentum generation process as will be more fully described herein below. The orbital angular momentum twisted waves 1108 are applied to a sample material 1110 under test. The sample material 1110 contains a material, and the concentration of the material is determined via a concentration detection apparatus in accordance with the process described herein.

A series of output waves 1112 from the sample material 1110 exit the sample and have a particular orbital angular momentum imparted thereto as a result of the concentration of the particular material under study within the sample material 1110. The output waves 1112 are applied to a matching module 1114 that includes a mapping aperture for amplifying a particular orbital angular momentum generated by the specific material under study. The matching module 1114 will amplify the orbital angular momentums associated with the particular concentration of material that is detected by the apparatus. The amplified OAM waves 1116 are provided to a detector 1118. The detector 1118 detects OAM waves relating to the concentration of a material within the sample and provides this concentration information to a user interface/processor 1120. The user interface/processor 1120 interprets the concentration information and provides relevant concentration indication to an individual or a recording device.

Figure 12:
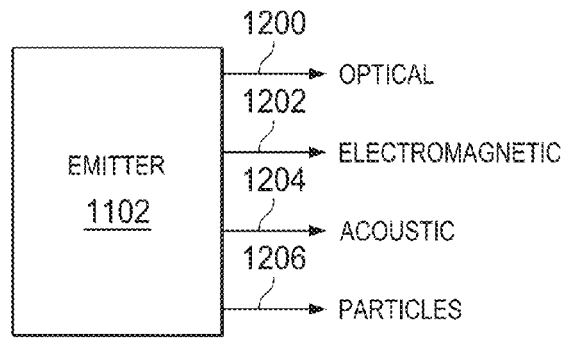
FIG. 12 illustrates an emitter of the system of FIG. 11.

Referring now to FIG. 12, there is more particularly illustrated the emitter 1102. The emitter 1102 may emit a number of types of energy waves 1104 to the OAM generation module 1106. The emitter 1102 may emit optical waves 1200, electromagnetic waves 1202, acoustic waves 1204 or any other type of particle waves 1206. The emitted waves 1104 are plane waves such as those illustrated in FIG. 7 having no orbital angular momentum applied thereto and may come from a variety of types of emission devices and have information included therein. In one embodiment, the emission device may comprise a laser. Plane waves have wavefronts that are parallel to each other having no twist or helicity applied thereto, and the orbital angular momentum of the wave is equal to 0. The Poynting vector within a plane wave is completely in line with the direction of propagation of the wave.

Figure 13:
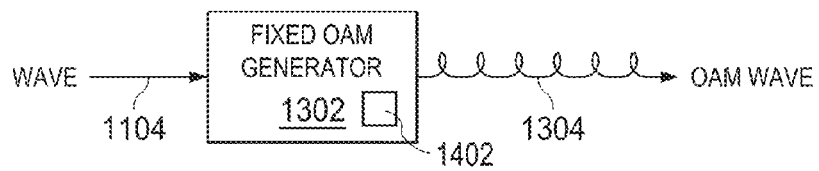
FIG. 13 illustrates a fixed orbital angular momentum generator of the system of FIG. 11.
Figure 14A:
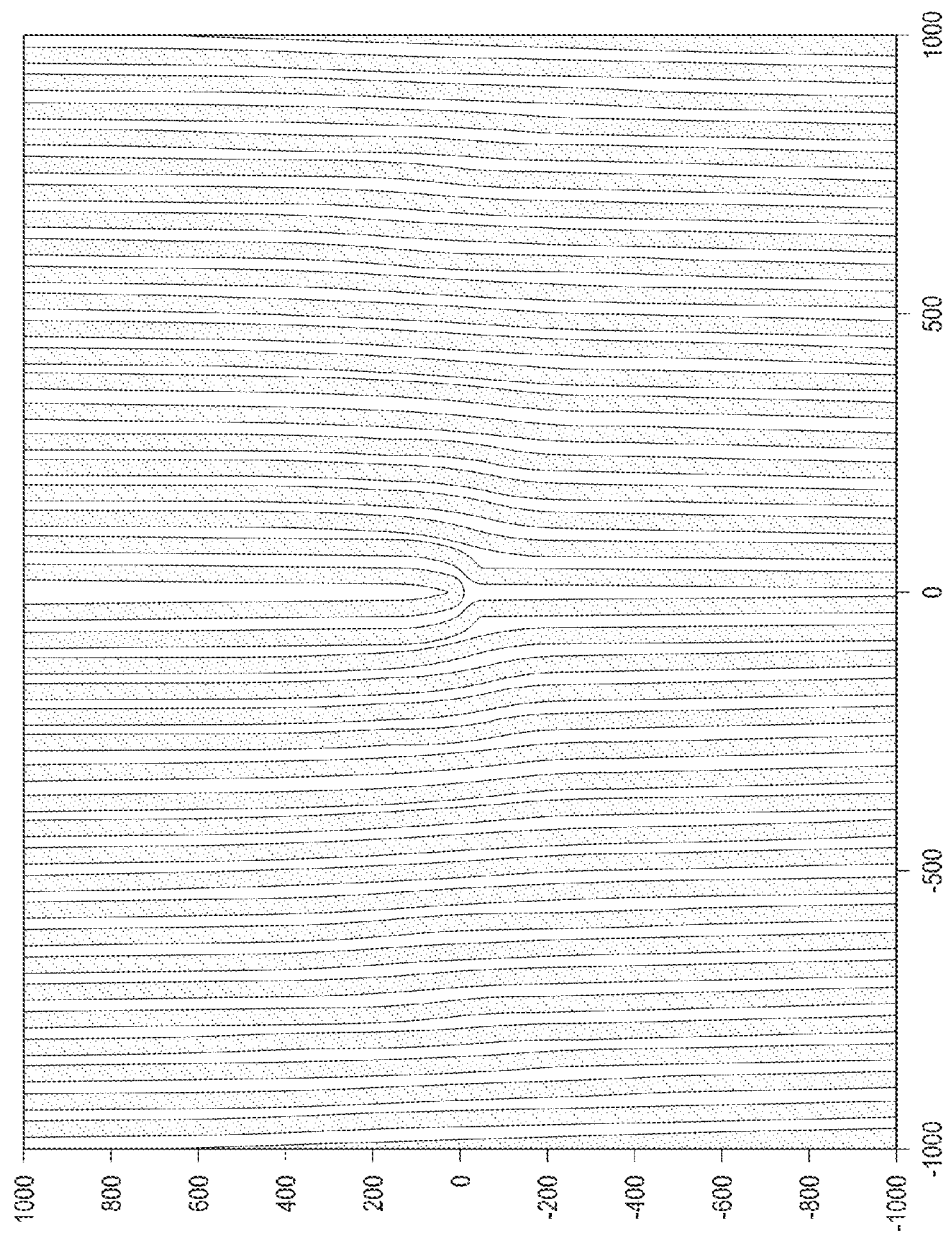
FIGS. 14a-14d illustrate various holograms for use in applying an orbital angular momentum to a plane wave signal.
Figure 14B:
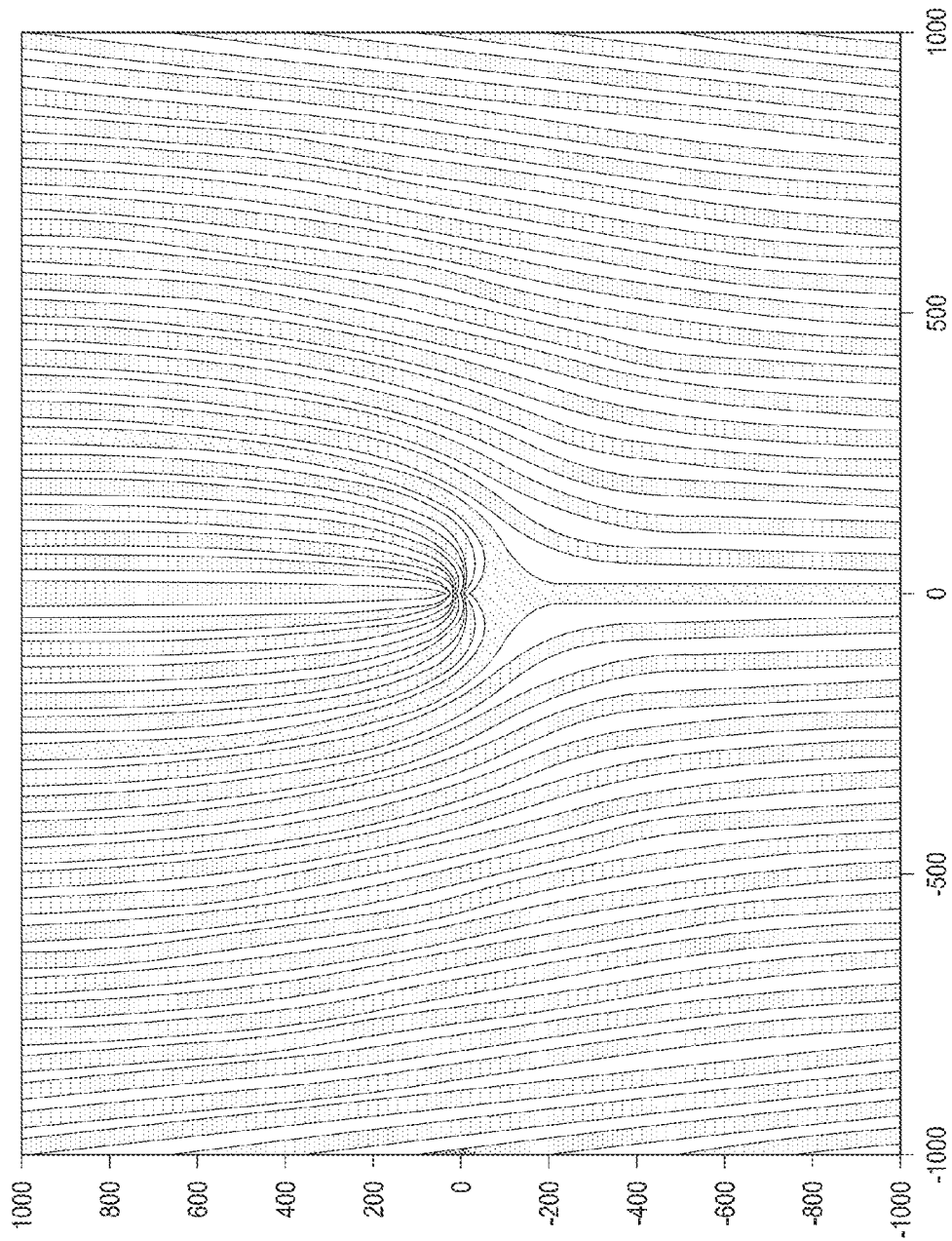
Figure 14C:
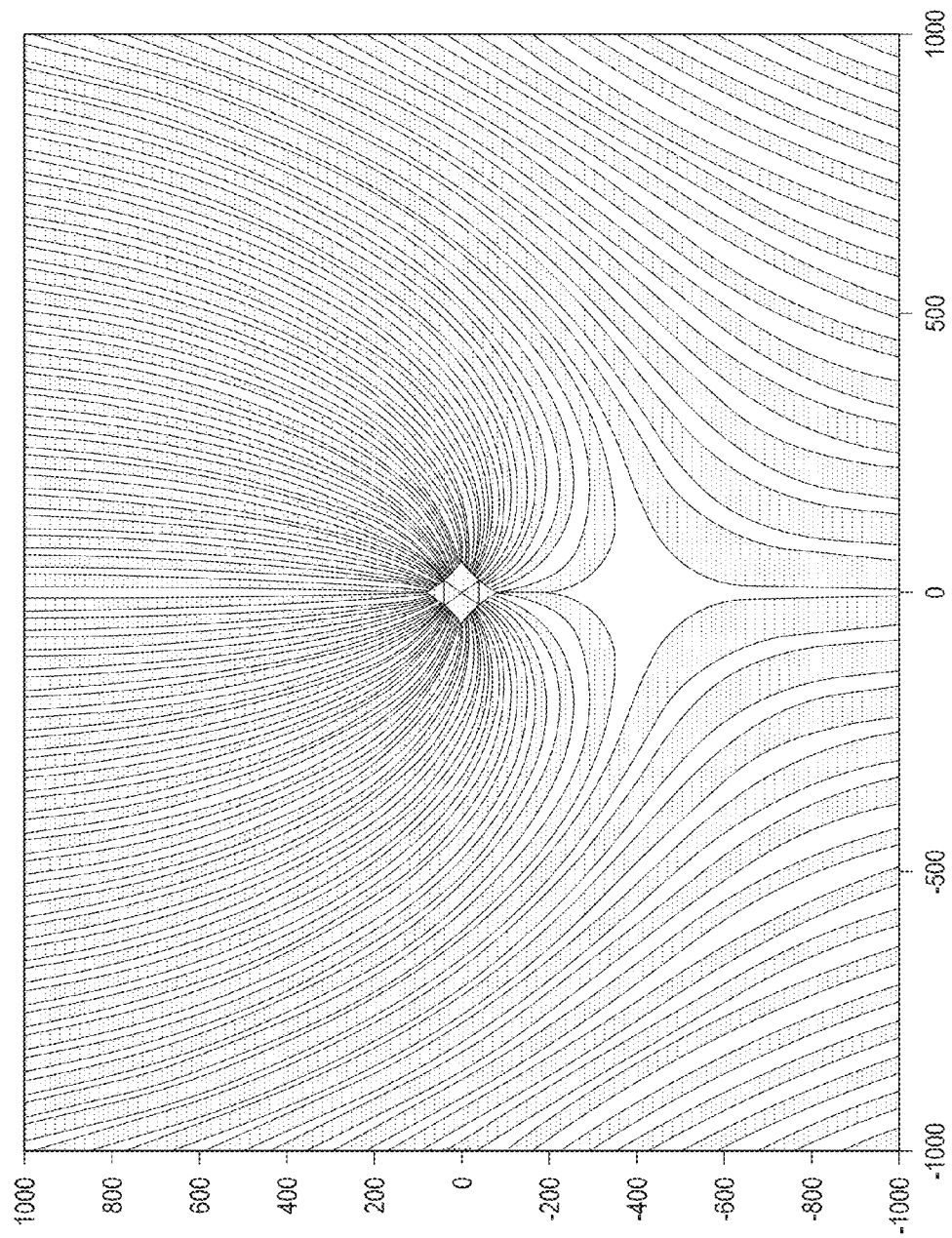
Figure 14D:
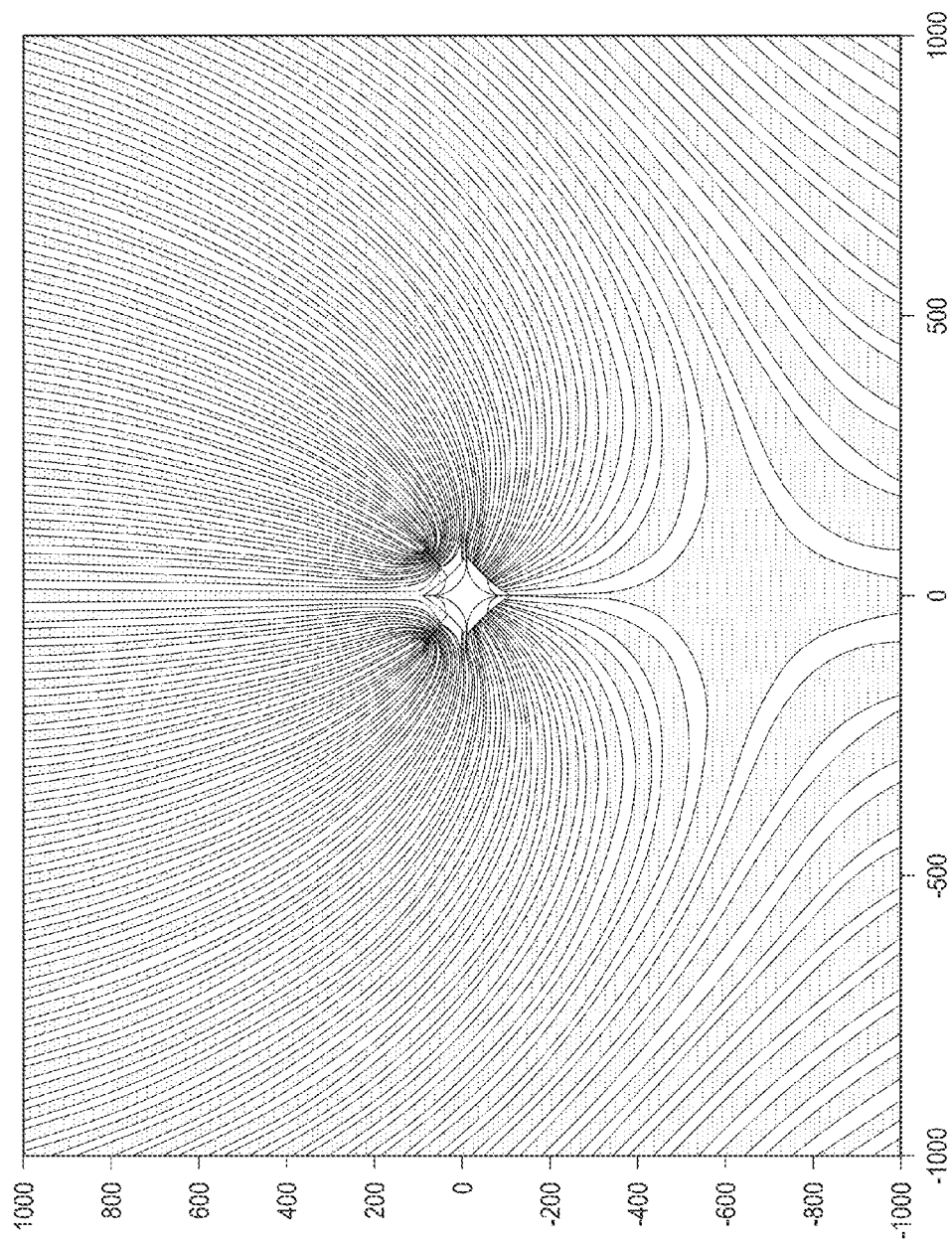

The OAM generation module 1106 processes the incoming plane wave 1104 and imparts a known orbital angular momentum onto the plane waves 1104 provided from the emitter 1102. The OAM generation module 1106 generates twisted or helical electromagnetic, optic, acoustic or other types of particle waves from the plane waves of the emitter 702. A helical wave 1108 is not aligned with the direction of propagation of the wave but has a procession around direction of propagation as shown in FIG. 5. The OAM generation module 1106 may comprise in one embodiment a fixed orbital angular momentum generator 1302 as illustrated in FIG. 13. The fixed orbital angular momentum generator 1302 receives the plane waves 1104 from the emitter 1102 and generates an output wave 1304 having a fixed orbital angular momentum applied thereto.

The fixed orbital angular momentum generator 1302 may in one embodiment comprise a holographic image for applying the fixed orbital angular momentum to the plane wave 1104 in order to generate the OAM twisted wave 904. Various types of holographic images may be generated in order to create the desired orbital angular momentum twist to an optical signal that is being applied to the orbital angular momentum generator 1102. Various examples of these holographic images are illustrated in FIG. 14a-14d. In one embodiment, the conversion of the plane wave signals transmitted from the emitter 1102 by the orbital angular momentum generation circuitry 706 may be achieved using holographic images.

Figure 15:
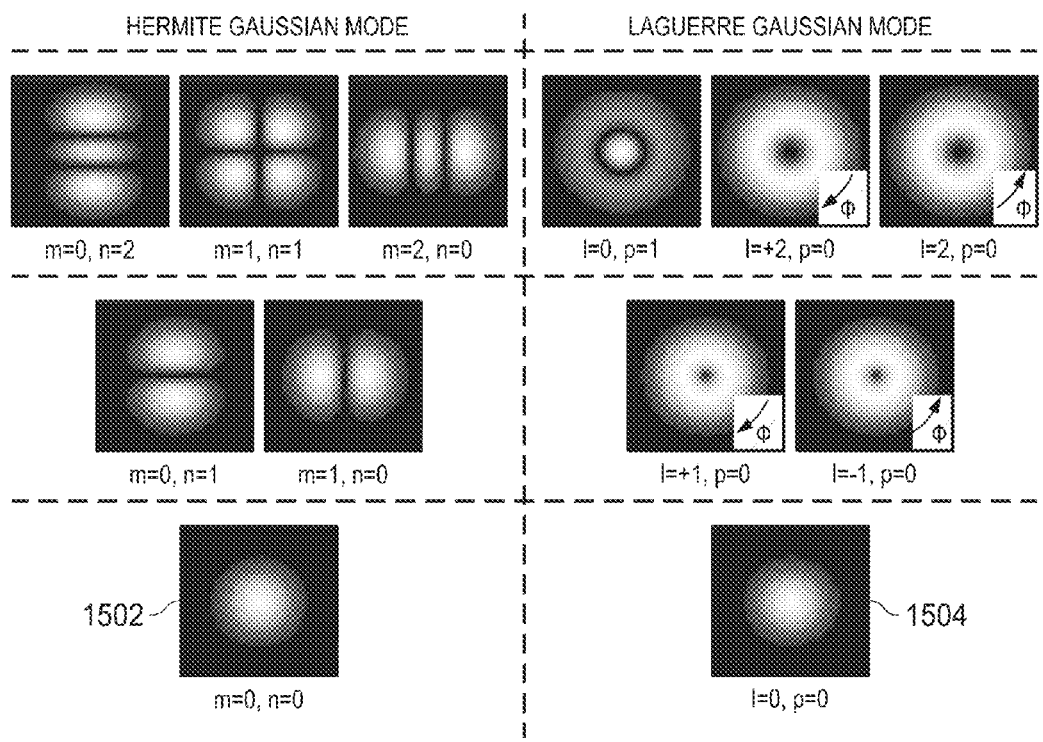
FIG. 15 illustrates the relationship between Hermite-Gaussian modes and Laguerre-Gaussian modes.

Most commercial lasers emit an $HG_{00}$ (Hermite-Gaussian) mode 1502 (FIG. 15) with a planar wave front and a transverse intensity described by a Gaussian function. Although a number of different methods have been used to successfully transform an $HG_{00}$ Hermite-Gaussian mode 1502 into a Laguerre-Gaussian mode 1504, the simplest to understand is the use of a hologram.

The cylindrical symmetric solution $u_{pl}(r,\phi,z)$ which describes Laguerre-Gaussian beams, is given by the equation:

$$u_{pl}(r,\phi,z) = \frac{C}{(1+z^2/z_R^2)^{1/2}} \left[\frac{r\sqrt{2}}{w(z)}\right]^l L_p^l\left[\frac{2r^2}{w^2(z)}\right] \exp\left[\frac{-r^2}{w^2(z)}\right]$$

$$\exp\left[\frac{-ikr^2z}{2(z^2+z_R^2)}\right] \exp(-il\phi) \times \exp\left[i(2p+l+1)\tan^{-1}\frac{z}{z_R}\right]$$

Where $z_R$ is the Rayleigh range, $w(z)$ is the radius of the beam, $L_P$ is the Laguerre polynomial, C is a constant, and the beam waist is at z=0.

In its simplest form, a computer generated hologram is produced from the calculated interference pattern that results when the desired beam intersects the beam of a conventional laser at a small angle. The calculated pattern is transferred to a high resolution holographic film. When the developed hologram is placed in the original laser beam, a diffraction pattern results. The first order of which has a desired amplitude and phase distribution. This is one manner for implementing the OAM generation module 1106. A number of examples of holographic images for use within a OAM generation module are illustrated with respect to FIGS. 14a-14e.

There are various levels of sophistication in hologram design. Holograms that comprise only black and white areas with no grayscale are referred to as binary holograms. Within binary holograms, the relative intensities of the two interfering beams play no role and the transmission of the hologram is set to be zero for a calculated phase difference between zero and π, or unity for a phase difference between π and 2π. A limitation of binary holograms is that very little of the incident power ends up in the first order diffracted spot, although this can be partly overcome by blazing the grating. When mode purity is of particular importance, it is also possible to create more sophisticated holograms where the contrast of the pattern is varied as a function of radius such that the diffracted beam has the required radial profile.

A plane wave shining through the holographic images 1402 will have a predetermined orbital angular momentum shift applied thereto after passing through the holographic image 1402. OAM generator 1302 is fixed in the sense that a same image is used and applied to the beam being passed through the holographic image. Since the holographic image 1402 does not change, the same orbital angular momentum is always applied to the beam being passed through the holographic image 1402. While FIG. 14a-14e illustrate a number of embodiments of various holographic images that might be utilized within the orbital angular momentum generator 1302, it will be realized that any type of holographic image 1402 may be utilized in order to achieve the desired orbital angular momentum within an beam being shined through the image 1402.

Figure 16:
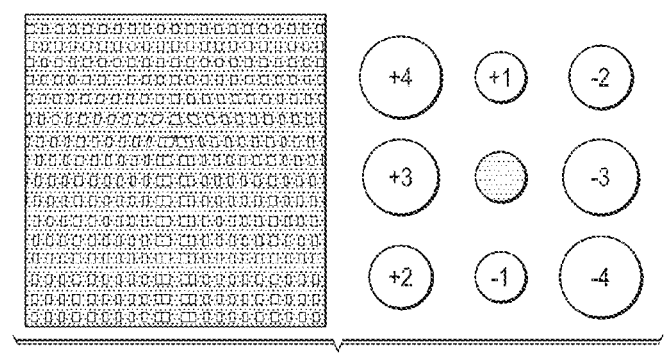
FIG. 16 illustrates super-imposed holograms for applying orbital angular momentum to a signal.

In another example of a holographic image illustrated in FIG. 16, there is illustrated a hologram that utilizes two separate holograms that are gridded together to produce a rich number of orbital angular momentum (l). The superimposed holograms of FIG. 16 have an orbital angular momentum of l=1 and l=3 which are superimposed upon each other to compose the composite vortex grid 1602. The holograms utilized may also be built in a manner that the two holograms are gridded together to produce a varied number of orbital angular momentums (l) not just on a line (l=+1, l=0, l=−1) but on a square which is able to identify the many variables more easily. Thus, in the example in FIG. 16, the orbital angular momentums along the top edge vary from +4 to +1 to −2 and on the bottom edge from +2 to −1 to −4. Similarly, along the left edge the orbital angular momentums vary from +4 to +3 to +2 and on the right edge from −2 to −3 to −4. Across the horizontal center of the hologram the orbital angular momentums provided vary from +3 to 0 to −3 and along the vertical axis vary from +1 to 0 to −1. Thus, depending upon the portion of the grid a beam may pass through, varying orbital angular momentum may be achieved.

Figure 17:
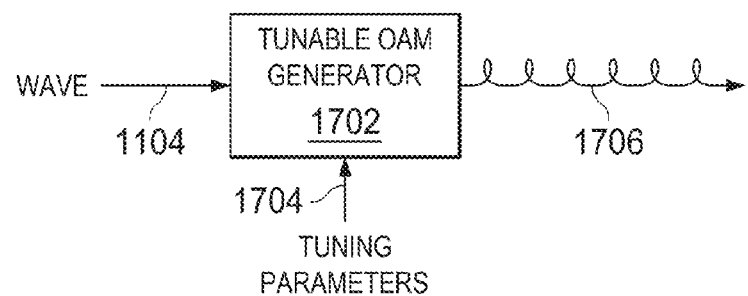
FIG. 17 illustrates a tunable orbital angular momentum generator for use in the system of FIG. 11.

Referring now to FIG. 17, in addition to a fixed orbital angular momentum generator, the orbital angular momentum generation circuitry 1106 may also comprise a tunable orbital angular momentum generator circuitry 1702. The tunable orbital angular momentum generator 1702 receives the input plane wave 1104 but additionally receives one or more tuning parameters 1704. The tuning parameters 1704 tune the tunable OAM generator 1702 to apply a selected orbital angular momentum so that the tuned OAM wave 1706 that is output from the OAM generator 1702 has a selected orbital angular momentum value applied thereto.

This may be achieved in any number of fashions. In one embodiment, illustrated in FIG. 18, the tunable orbital angular momentum generator 1702 may include multiple hologram images 1802 within the tunable OAM generator 1702. The tuning parameters 1704 enable selection of one of the holographic images 1806 in order to provide the desired OAM wave twisted output signal 1706 through a selector circuit 1804. Alternatively, the gridded holographic image such as that described in FIG. 16 may be utilized and the beam shined on a portion of the gridded image to provide the desired OAM output. The tunable OAM generator 1702 has the advantage of being controlled to apply a particular orbital angular momentum to the output orbital angular momentum wave 1706 depending upon the provided input parameter 1704. This enables the concentrations of a variety of different materials to be monitored, or alternatively, for various different concentrations of the same material to be monitored.

Figure 18:
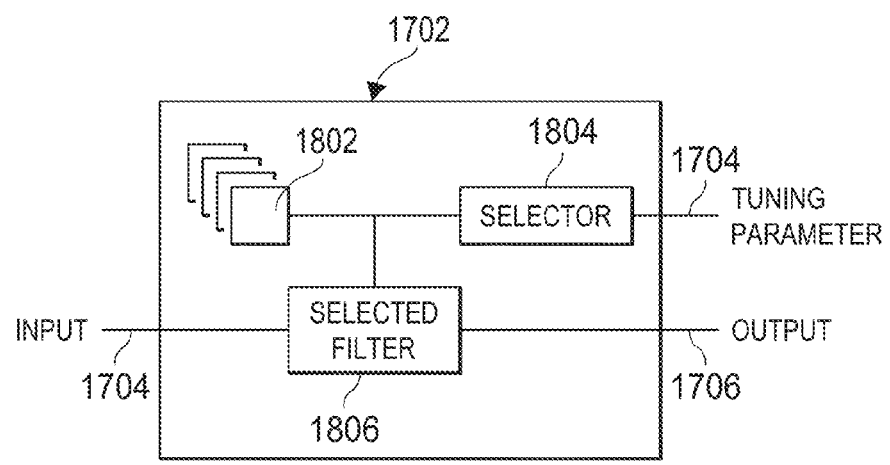
FIG. 18 illustrates a block diagram of a tunable orbital angular momentum generator including multiple hologram images therein.

Referring now to FIG. 18, there is more particularly implemented a block diagram of a tunable orbital angular momentum generator 1702. The generator 1702 includes a plurality of holographic images 1802 for providing orbital angular momentums of various types to a provided light signal. These holographic images 1802 are selected responsive to a selector circuitry 1804 that is responsive to the input tuning parameters 1704. The selected filter 1806 comprises the holographic image that has been selected responsive to the selector controller 1804 and receives the input plane waves 1104 to provide the tuned orbital angular momentum wave output 1706. In this manner, signals having a desired orbital angular momentum may be output from the OAM generation circuitry 1106.

Figure 19:
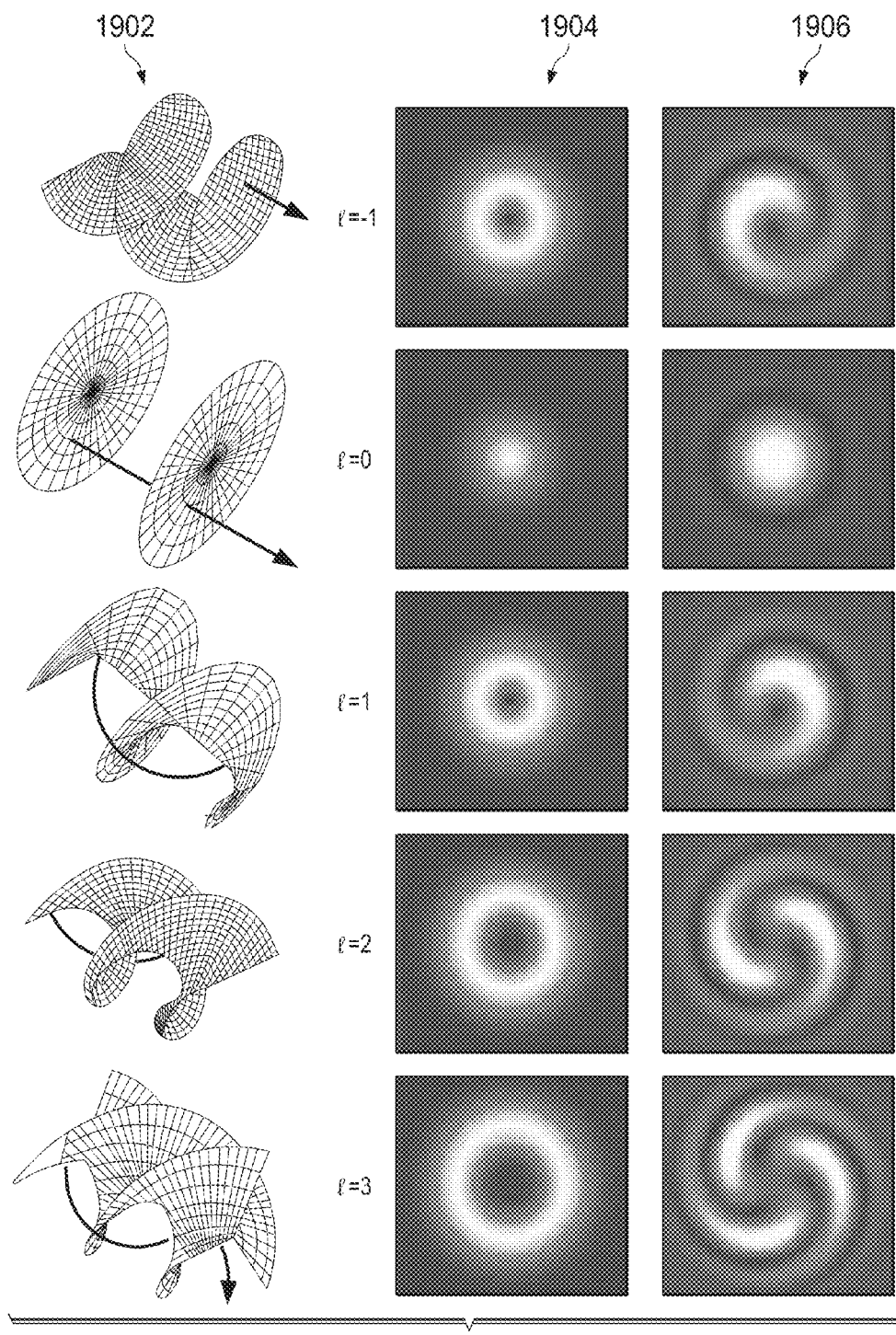
FIG. 19 illustrates the manner in which the output of the OAM generator may be varied by applying different orbital angular momentums thereto.

Referring now to FIG. 19, there is illustrated the manner in which the output of the OAM generator 1106 may vary a signal by applying different orbital angular momentum thereto. FIG. 19 illustrates helical phase fronts in which the Poynting vector is no longer parallel to the beam axis and thus has an orbital angular momentum applied thereto. In any fixed radius within the beam, the Poynting vector follows a spiral trajectory around the axis. Rows are labeled by 1, the orbital angular momentum quantum number, L=1$\hbar$ is the beams orbital angular momentum per photon within the output signal. For each l, the left column 1902 is the light beam's instantaneous phase. The center column 1904 comprises the angular intensity profiles and the right column 1906 illustrates what occurs when such a beam interferes with a plane wave and produces a spiral intensity pattern. This is illustrated for orbital angular momentums of −1, 0, 1, 2 and 3 within the various rows of FIG. 19.

Figure 20:
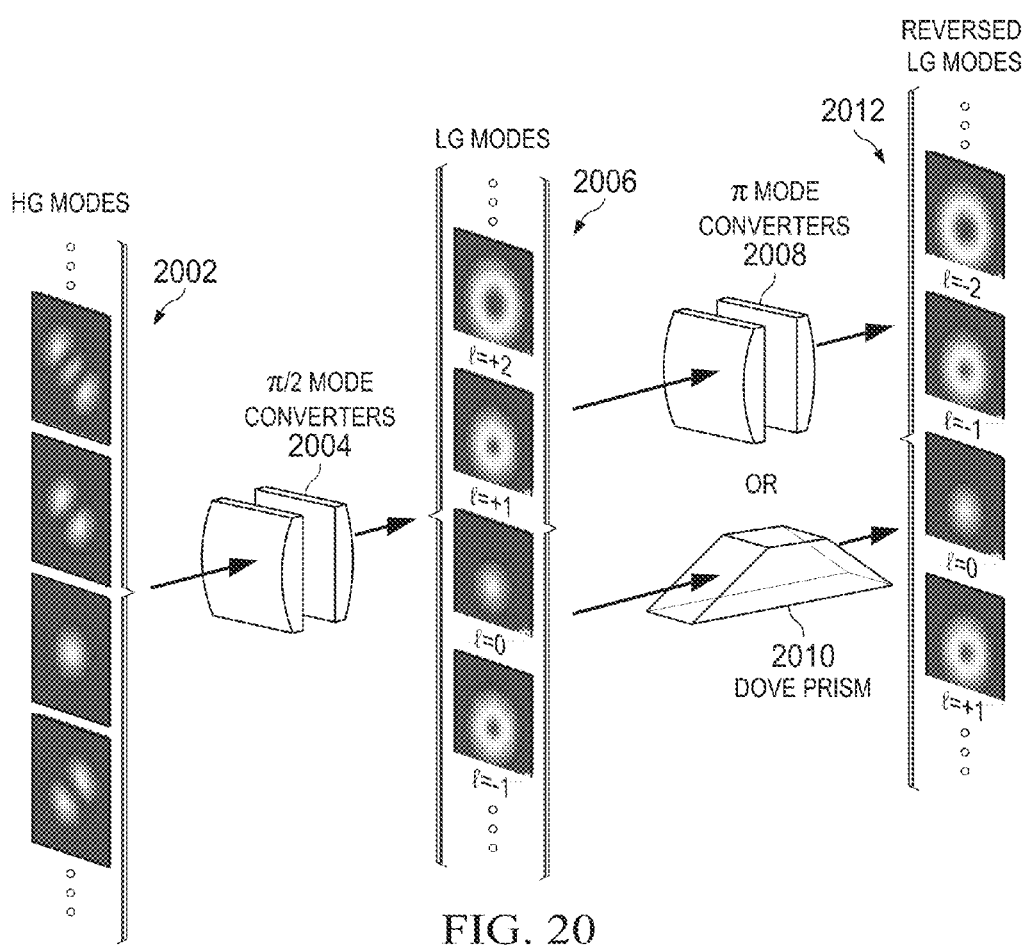
FIG. 20 illustrates an alternative manner in which the OAM generator may convert a Hermite-Gaussian beam to a Laguerre-Gaussian beam.

Referring now to FIG. 20, there is illustrated an alternative manner in which the OAM generator 1106 may convert a Hermite-Gaussian beam output from an emitter 1102 to a Laguerre-Gaussian beams having imparted therein an orbital angular momentum using mode converters 2004 and a Dove prism 2010. The Hermite-Gaussian mode plane waves 2002 are provided to a $\pi/2$ mode convertor 2004. The n/2 mode convertor 2004 produce beams in the Laguerre-Gaussian modes 2006. The Laguerre-Gaussian modes beams 2006 are applied to either a it mode convertor 2008 or a dove prism 2010 that reverses the mode to create a reverse Laguerre-Gaussian mode signal 2012.

Figure 21:
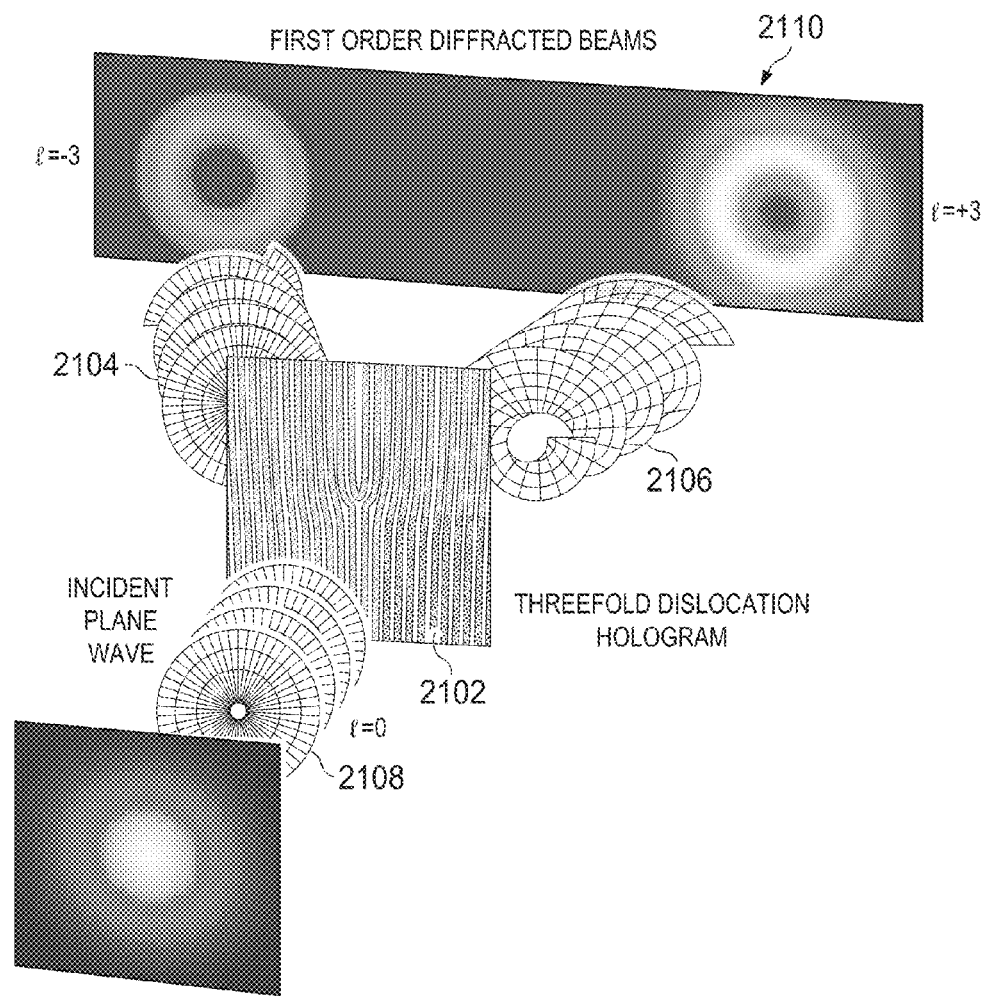
FIG. 21 illustrates the manner in which holograms within an OAM generator may twist a beam of light.

Referring now to FIG. 21, there is illustrated the manner in which holograms within the OAM generator 1106 generate a twisted light beam. A hologram 2102 can produce light beam 2104 and light beam 2106 having helical wave fronts and associated orbital angular momentum lh per photon. The appropriate hologram 2102 can be calculated or generated from the interference pattern between the desired beam form 2104, 2106 and a plane wave 2108. The resulting holographic pattern within the hologram 2102 resembles a diffraction grating, but has a 1-pronged dislocation at the beam axis. When the hologram is illuminated with the plane wave 2108, the first-order diffracted beams 2104 and 2106 have the desired helical wave fronts to provide the desired first ordered diffracted beam display 2110.

Figure 22:
FIG. 22 illustrates the manner in which a sample receives an OAM twisted wave and provides an output wave having a particular OAM signature.

Referring now to FIG. 22, there is more particularly illustrated the manner in which the sample 1110 receives the input OAM twisted wave 1108 provided from the OAM generator 1106 and provides an output OAM wave 1112 having a particular OAM signature associated therewith that depends upon the concentration of a particular monitored material within the sample 1110. The sample 1110 may comprise any sample that is under study and may be in a solid form, liquid form or gas form. The sample material 1110 that may be detected using the system described herein may comprise a variety of different materials. As stated previously, the material may comprise liquids such as blood, water, oil or chemicals. The various types of carbon bondings such as C—H, C—O, C—P, C—S or C—N may be provided for detection. The system may also detect various types of bondings between carbon atoms such as a single bond (methane or Isooctane), dual bond items (butadiene and benzene) or triple bond carbon items such as acetylene.

The sample 1110 may include detectable items such as organic compounds including carbohydrates, lipids (cylcerol and fatty acids), nucleic acids (C,H,O,N,P) (RNA and DNA) or various types of proteins such as polyour of amino $NH_2$ and carboxyl COOH or aminos such as tryptophan, tyrosine and phenylalanine Various chains within the samples 1110 may also be detected such as monomers, isomers and polymers. Enzymes such as ATP and ADP within the samples may be detected. Substances produced or released by glands of the body may be in the sample and detected. These include items released by the exocrine glands via tube/ducts, endocrine glands released directly into blood samples or hormones. Various types of glands that may have their secretions detected within a sample 1110 include the hypothalamus, pineal and pituitary glands, the parathyroid and thyroid and *thymus*, the adrenal and pancreas glands of the torso and the hormones released by the ovaries or testes of a male or female.

The sample 1110 may also be used for detecting various types of biochemical markers within the blood and urine of an individual such as melanocytes and keratinocytes. The sample 1110 may include various parts of the body to detect defense substances therein. For example, with respect to the skin, the sample 1110 may be used to detect carotenoids, vitamins, enzymes, b-carotene and lycopene. With respect to the eye pigment, the melanin/eumelanin, dihydroxyindole or carboxylic may be detected. The system may also detect various types of materials within the body's biosynthetic pathways within the sample 1110 including hemoglobin, myoglobin, cytochromes, and porphyrin molecules such as protoporphyrin, coporphyrin, uroporphyrin and nematoporphyrin. The sample 1110 may also contain various bacterias to be detected such as propion bacterium, *acnes*. Also various types of dental plaque bacteria may be detected such as porphyromonos gingivitis, *prevotella* intremedi and *prevotella nigrescens*. The sample 1110 may also be used for the detection of glucose in insulin within a blood sample 1110.

Figure 23:
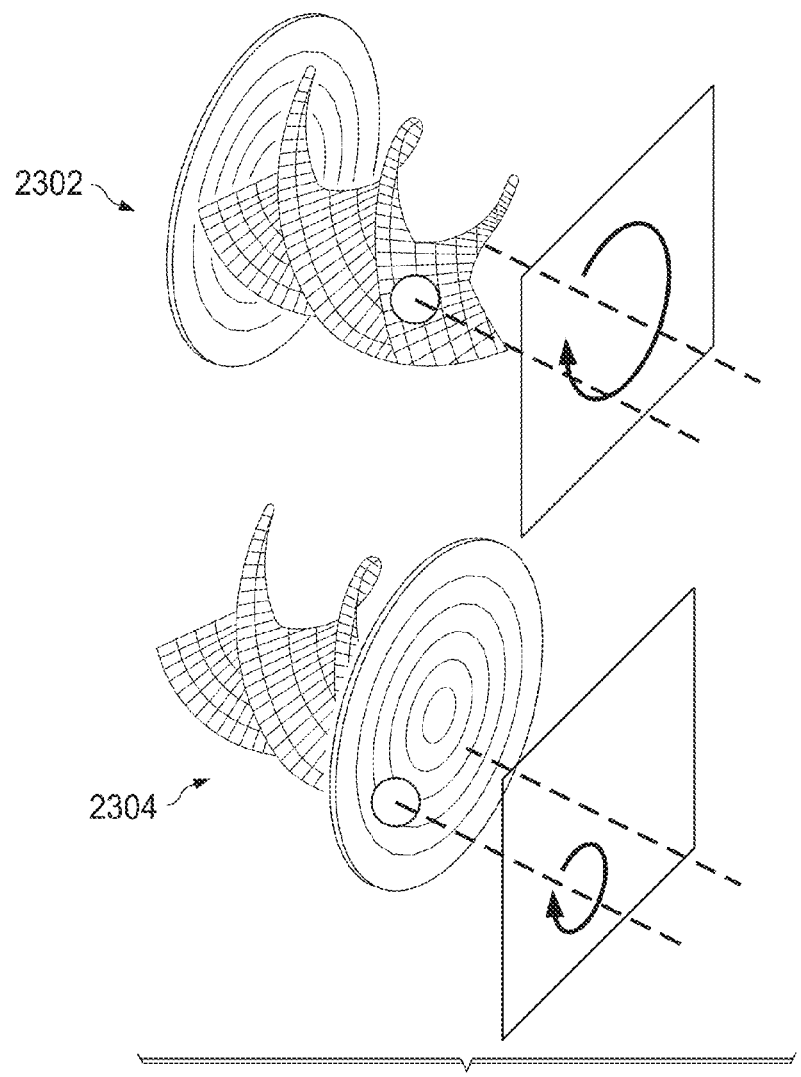
FIG. 23 illustrates the manner in which orbital angular momentum interacts with a molecule around its beam axis.

The orbital angular momentum within the beams provided within the sample 1110 may be transferred from light to matter molecules depending upon the rotation of the matter molecules. When a circularly polarized laser beam with a helical wave front traps a molecule in an angular ring of light around the beam axis, one can observe the transfer of both orbital and spin angular momentum. The trapping is a form of optical tweezing accomplished without mechanical constraints by the ring's intensity gradient. The orbital angular momentum transferred to the molecule makes it orbit around the beam axis as illustrated at 2302 of FIG. 23. The spin angular momentum sets the molecule spinning on its own axis as illustrated at 2304.

The output OAM wave 1112 from the sample 1110 will have an orbital angular momentum associated therewith that is different from the orbital angular momentum provided on the input OAM wave 1108. The difference in the output OAM wave 1112 will depend upon the material contained within the sample 1110 and the concentration of these materials within the sample 1110. Differing materials of differing concentration will have unique orbital angular momentums associated therewith. Thus, by analyzing the particular orbital angular momentum signature associated with the output OAM wave 1112, determinations may be made as to the materials present within the sample 1110 and the concentration of these materials within the sample may also be determined.

Figure 24:
FIG. 24 illustrates a block diagram of the matching circuitry for amplifying a received orbital angular momentum signal.

Referring now to FIG. 24, the matching module 1114 receives the output orbital angular momentum wave 1112 from the sample 1110 that has a particular signature associated therewith based upon the orbital angular momentum imparted to the waves passing through the sample 1110. The matching module 1114 amplifies the particular orbital angular momentum of interest in order to provide an amplified wave having the desired orbital angular momentum of interest 2416 amplified. The matching module 1114 may comprise a matching aperture that amplifies the detection orbital angular momentum associated with a specific material or characteristic that is under study. The matching module 1114 may in one embodiment comprise a holographic filter such as that described with respect to FIGS. 14a-14d in order to amplify the desired orbital angular momentum wave of interest. The matching module 1114 is established based upon a specific material of interest that is trying to be detected by the system. The matching module 1114 may comprise a fixed module using holograms as illustrated in FIGS. 14a-14d or a tunable module in a manner similar to that discussed with respect to the OAM generation module 1106. In this case, a number of different orbital angular momentums could be amplified by the matching module in order to detect differing materials or differing concentration of materials within the sample 1110. Other examples of components for the matching module 1114 include the use of quantum dots, nanomaterials or metamaterials in order to amplify any desired orbital angular momentum values within a received wave form from the sample 1110.

Figure 25:
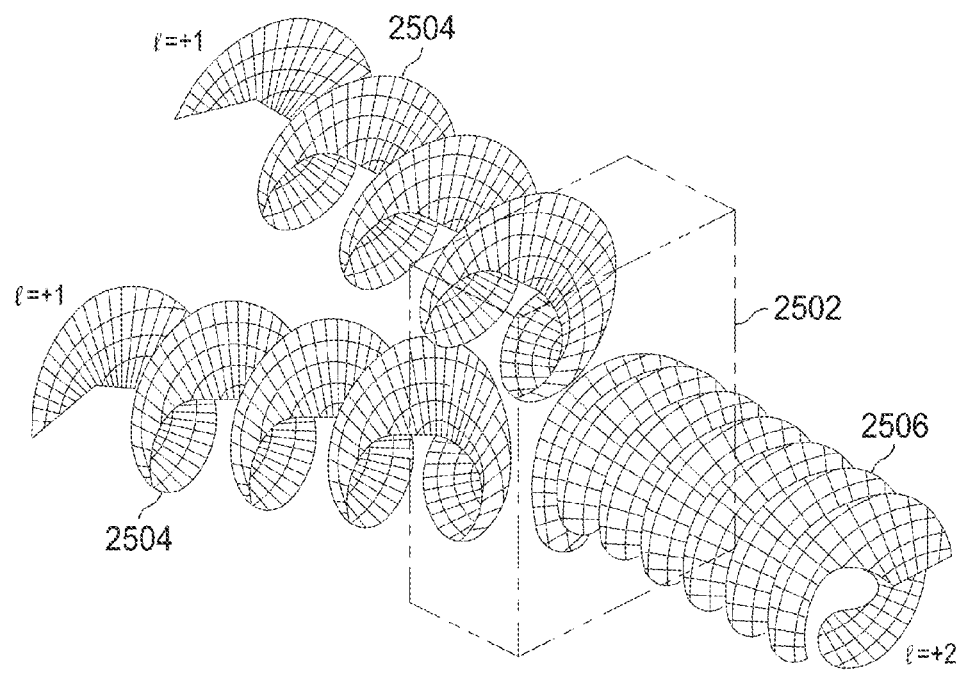
FIG. 25 illustrates the manner in which the matching module may use non-linear crystals in order to generate a higher order orbital angular momentum light beam.

Referring now to FIG. 25, the matching module 1114 rather than using holographic images in order to amplify the desired orbital angular momentum signals may use non-linear crystals in order to generate higher orbital angular momentum light beams. Using a non-linear crystal 2502, a first harmonic orbital angular momentum beam 2504 may be applied to a non-linear crystal 2502. The non-linear crystal 2502 will create a second order harmonic signal 2506.

Figure 26:
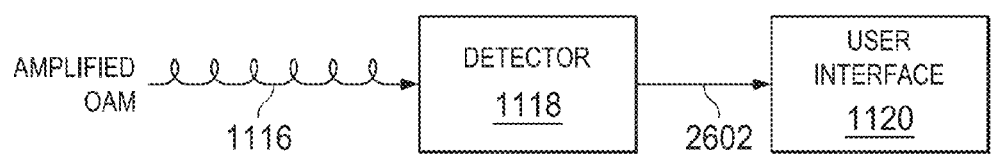
FIG. 26 illustrates a block diagram of an orbital angular momentum detector and user interface.

Referring now to FIG. 26, there is more particularly illustrated the detector 1118 to which the amplified orbital angular momentum wave 1116 from the matching circuit 1114 in order that the detector 1118 may extract desired OAM measurements 2602. The detector 1118 receives the amplified OAM waves 1116 and detects and measures observable changes within the orbital angular momentum of the emitted waves due to the concentration of a particular material under study within the sample 1110. The detector 1118 is able to measure observable changes within the emitted amplified OAM wave 1116 from the state of the input OAM wave 1108 applied to the sample 1110. The extracted OAM measurements 2602 are applied to the user interface 1120. The manner in which the detector 1118 may detect differences within the orbital angular momentum is more particularly illustrates with respect to FIG. 27-29.

Figure 27:
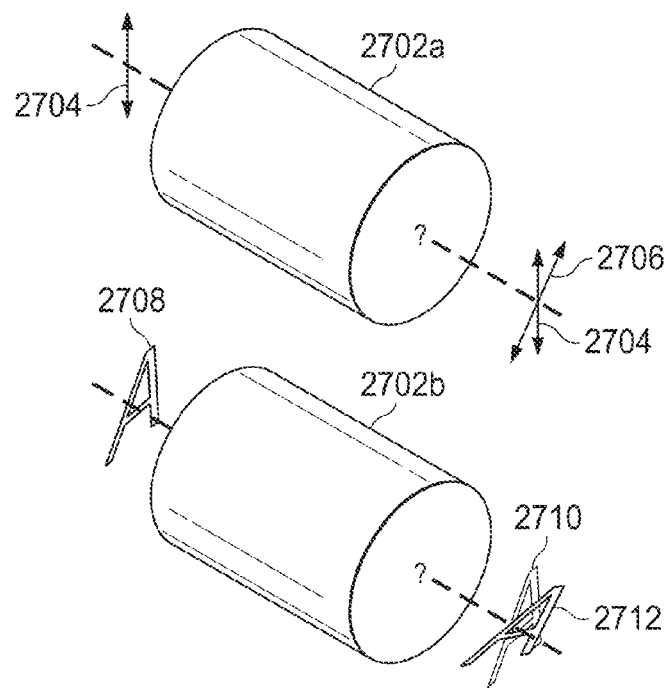
FIG. 27 illustrates the effect of sample concentrations upon the spin angular polarization and orbital angular polarization of a light beam passing through a sample.

FIG. 27 illustrates the difference in impact between spin angular polarization and orbital angular polarization due to passing of a beam of light through a sample 2702a/2702b. In sample 2702a, there is illustrated the manner in which spin angular polarization is altered responsive to a beam passing through the sample 2702a. The polarization of a wave having a particular spin angular momentum 2704 passing through the sample 2702a will rotate from a position 2704 to a new position 2706. The rotation occurs within the same plane of polarization. In a similar manner, as illustrated with respect to sample 2702b, an image appears as illustrated generally at 2708 before it passes through the sample 2702b. Upon passing the image through the sample 2702b the image will rotate from the position illustrated at 2710 to a rotated position illustrated at 2712. The amount of rotation is dependent upon the level of concentration of the material being detected within the sample 2702. Thus, as can be seen with respect to the sample 2702 of FIG. 27, both the spin angular polarization and the orbital angular momentum will change based upon the concentration of materials within the sample 2702. By measuring the amount of rotation of the image caused by the change in orbital angular momentum, the concentration of a particular material may be determined.

Figure 28:
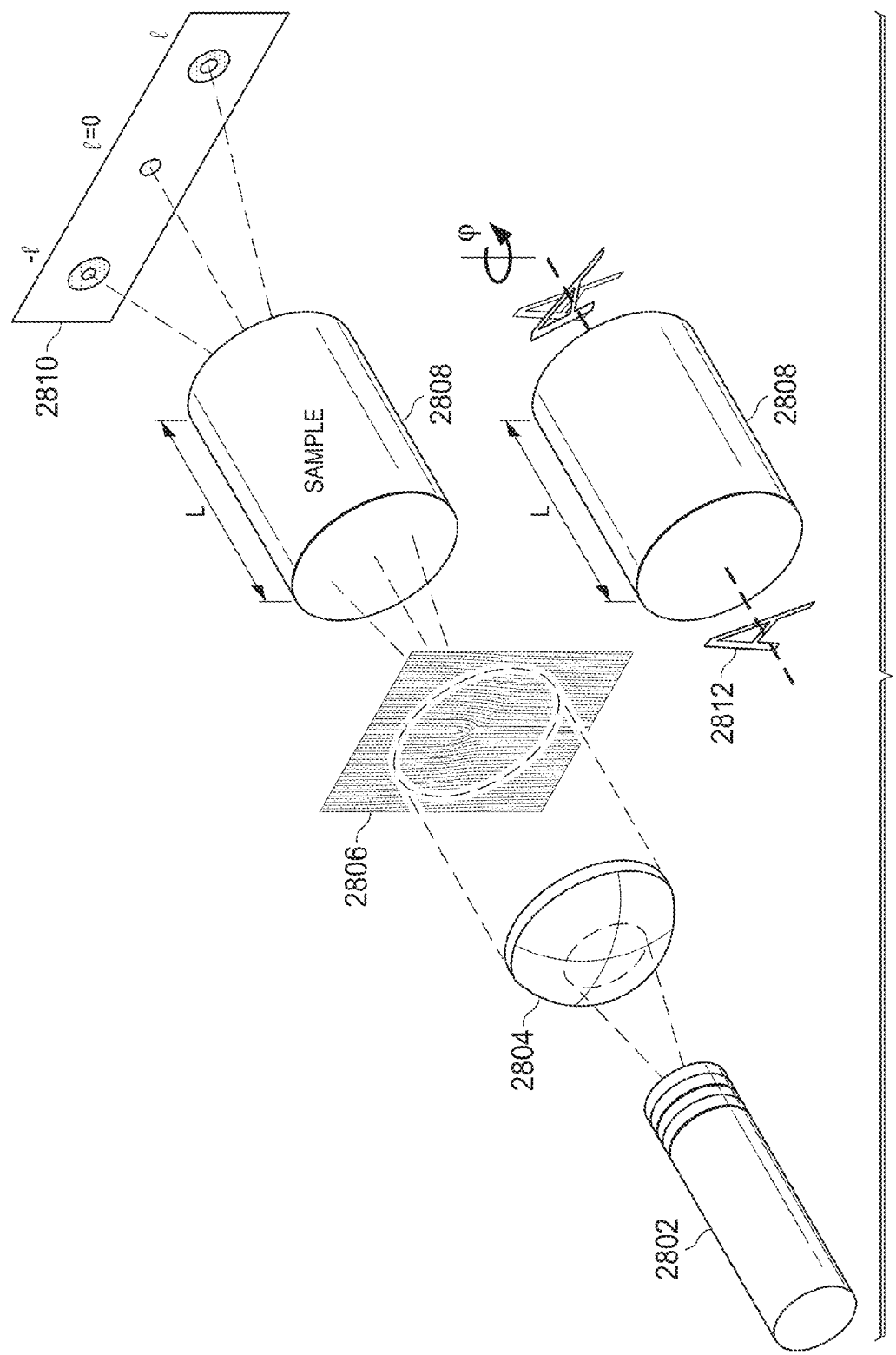
FIG. 28 more particularly illustrates the process that alters the orbital angular momentum polarization of a light beam passing through a sample.

This overall process can be more particularly illustrated in FIG. 28. A light source 2802 shines a light beam through expanding optics 2804. The expanded light beam is applied through a metalab generated hologram 2806 that imparts an orbital angular momentum to the beam. The twisted beam from the hologram 2806 is shined through a sample 2808 having a particular length L. This causes the generation of a twisted beam on the output side of the sample 2808 to create a number of detectable waves having various orbital angular momentums 2810 associated therewith. The image 2812 associated with the light beam that is applied to sample 2808 will rotate an angle φ depending upon the concentration of the material within the sample 2808. The rotation φ of the image 2812 is different for each value orbital angular momentum −l or +l. The change in rotation of the image Δφ may be described according to the equation:

$$\Delta\phi = \phi_l - \phi_{-l} = f(l, L, C)$$

Where l is orbital angular momentum number, L is the path length of the sample and C is the concentration of the material being detected.

Thus, since the length of the sample L is known and the orbital angular momentum may be determined using the process described herein, these two pieces of information may be able to calculate a concentration of the material within the provided sample.

Figure 29:
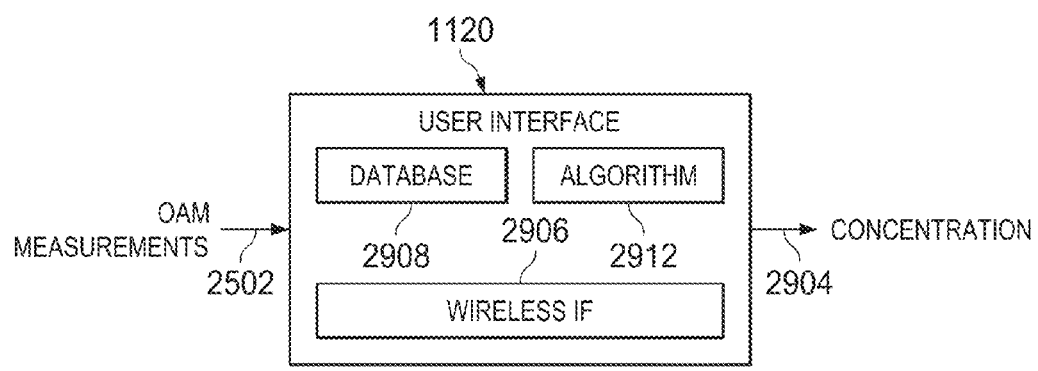
FIG. 29 provides a block diagram of a user interface of the system of FIG. 11.

The above equation may be utilized within the user interface more particularly illustrated in FIG. 29. The user interface/processor 1120 processes the OAM measurements 2502 using an internal algorithm 2912 that provides for the generation of concentration information 2904 that may be displayed in some type of user display. The algorithm would in one embodiment utilize that equation described herein above in order to determine the concentration based upon the length of a sample and the detected variation in orbital angular momentum. The process for calculating the concentration may be done in a laboratory setting where the information is transmitted wirelessly to the lab or the user interface can be associated with a wearable device connected to a meter or cell phone running an application on the cell phone connected via a local area network or wide area network to a personal or public cloud. The user interface 1120 of the device can either have a wired or wireless connection utilizing Bluetooth, ZigBee or other wireless protocols.

Figure 30:
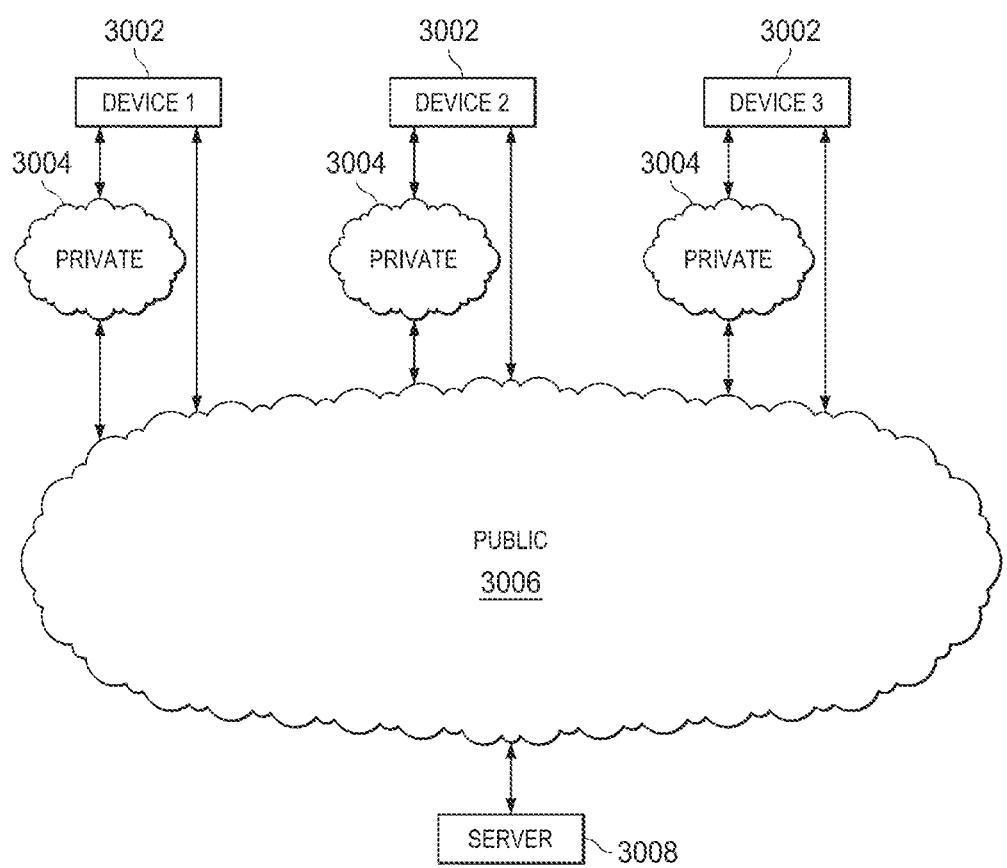
FIG. 30 illustrates a network configuration for passing around data collected via devices such as that illustrated in FIG. 11.

Referring now to FIG. 30, there is illustrated the manner in which the various data accumulated within the user interface 1120 that has been collected in the manner described herein above may be stored and utilized for higher level analysis. Various devices 3002 for collecting data as described herein above may communicate via private network clouds 3004 or with a public cloud 3006. When communicating with a private cloud 3004, the devices 3002 merely store information that is associated with a particular user device that is for use with respect to analysis of the user associated with that user device. Thus, an individual user could be monitoring and storing information with respect to their present glucose concentrations in order to monitor and maintain their diabetes.

Alternatively, when information is compiled from multiple devices 3002 within the public cloud 3006, this information may be provided directly to the public cloud 3006 from the individual devices 3002 or through the private clouds 3004 of the associated network devices 3002. Utilizing this information within the public cloud 3006 large databases may be established within servers 3008 associated with the public cloud 3006 to enable large scale analysis of various health related issues associated with the information processed from each of the individual devices 3002. This information may be used for analyzing public health issues.

Thus, the user interface 1120 in addition to including the algorithm 2912 for determining concentration information 2904 will include a wireless interface 2906 enabling the collected information to be wirelessly transmitted over the public or private cloud as described with respect to FIG. 30. Alternatively, the user interface may comprise a storage database 2908 enabling the collected information to be locally stored rather than transmitted wirelessly to a remote location.

Figure 31:
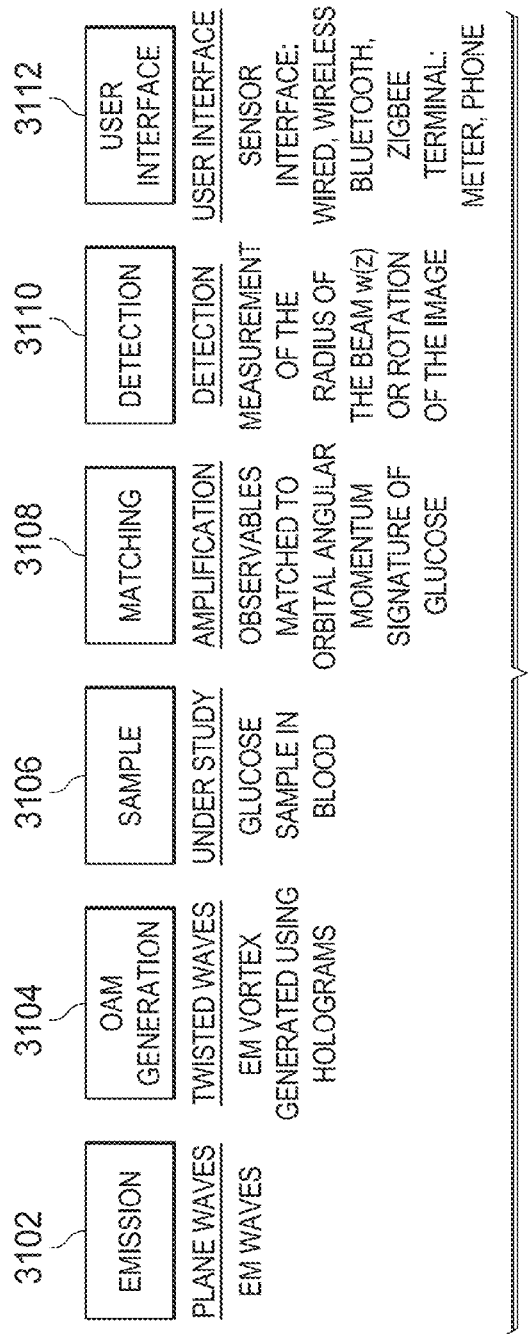
FIG. 31 provides a block diagram of a more particular embodiment of an apparatus for measuring the concentration of glucose using orbital angular momentum.

Referring now to FIG. 31, there is illustrated a particular example of a block diagram of a particular apparatus for measuring the concentration of glucose using the orbital angular momentum of photons of a light beam shined through a glucose sample. The process creates a second-order harmonic with helical light beam using a non-linear crystal such as that described with respect to FIG. 25. The emission module 3102 generates plain electromagnetic waves that are provided to an OAM generation module 3104. The OAM generation module 3104 generates light waves having an orbital angular momentum applied thereto using holograms to create a wave having an electromagnetic vortex. The OAM twisted waves are applied to the sample 3106 that is under study in order to detect the glucose concentration within a sample of blood. A rotated signature exits the sample 3106 in the manner described previously with respect to FIGS. 27-28 and is provided to the matching module 3108. The matching module 3108 will amplify the orbital angular momentum such that the observed concentrations may be calculated from the orbital momentum of the signature of the glucose. These amplified signals are provided to detection module 3110 which measures the radius of the beam w(z) or the rotation of the image provided to the sample via the light beam. This detected information is provided to the user interface that include a sensor interface wired or wireless Bluetooth or ZigBee connection to enable the provision of the material to a reading meter or a user phone for the display of concentration information with respect to the sample.

In this manner concentrations of various types of material as describe herein may be determined utilizing the orbital angular momentum signatures of the samples under study and the detection of these materials or their concentrations within the sample determine as described.

It will be appreciated by those skilled in the art having the benefit of this disclosure that this system and method for making concentration measurements within a sample material using orbital angular momentum provides a non-invasive manner for detecting material concentration. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An apparatus that measures a concentration of a material within a sample, comprising:
   signal generation circuitry that generates a first signal having at least one orbital angular momentum applied thereto and applying the first signal to the sample;
   a detector that receives the first signal after the first signal passes through the sample and that determines the concentration of the material within the sample based on a detected value of orbital angular momentum with the first signal received from the sample.

2. The apparatus of claim 1, wherein differing values of the concentration indicate different concentrations of the material within the sample.

3. The apparatus of claim 1, wherein the first signal comprises a light beam.

4. The apparatus of claim 1 further including amplifying circuitry that receives the first signal after the first signal passes through the sample and that amplifies a first portion of the first signal having the detected value of the orbital angular momentum associated therewith.

5. The apparatus of claim 1, wherein the detector further comprises:
   an orbital angular momentum detector that determines the detected value of the orbital angular momentum within the first signal from the sample; and
   a processor that determines the concentration of the material within the sample responsive to the detected value of the orbital angular momentum.

6. The apparatus of claim 1, wherein the signal generation circuitry further comprises:
   an emitting source that emits the first signal comprising a plurality of plane waves;
   orbital angular momentum generation circuitry that receives the first signal and that applies the at least one orbital angular momentum to the plane waves of the first signal.

7. The apparatus of claim 4, wherein the amplifying circuitry further includes a hologram that amplifies the orbital angular momentum associated with the concentration of the material in the sample.

8. The apparatus of claim 5 further including a user interface associated with the processor comprising:
   a set of computer instructions that configures the processor to determine the concentration of the material within the sample responsive to the detected value of the orbital angular momentum;

a database that stores concentration data from concentrations determined by the processor.

9. The apparatus of claim 8, wherein the user interface further includes a wireless interface that communicates the concentration data to a remote location.

10. The apparatus of claim 6, wherein the orbital angular momentum generation circuitry comprises a fixed orbital angular momentum generation circuitry that applies a fixed orbital angular momentum to the first signal.

11. The apparatus of claim 6, wherein the orbital angular momentum generation circuitry comprises a tunable orbital angular momentum generation circuitry that applies a selected orbital angular momentum to the first signal responsive to at least one tuning parameter provided to the tunable orbital angular momentum generation circuitry.

12. The apparatus of claim 6, wherein the orbital angular momentum generation circuitry comprises:
   at least one pi/2 mode converter that converts the first signal from Hermite-Guassian modes to Laguerre-Gaussian modes;
   a converter that converts the first signal in the Laguerre-Gaussian modes to reversed Laguerre-Gaussian modes.

13. The apparatus of claim 6, wherein the orbital angular momentum generation circuitry further includes a hologram that applies the at least one orbital angular momentum to the plane waves of the first signal.

14. The apparatus of claim 13, wherein the hologram comprise a pair of superimposed holograms comprising a composite vortex grid.

15. An apparatus that measures a concentration of a material within a sample, comprising:
   an emitting source that emits a first light beam comprising a plurality of plane waves;
   orbital angular momentum generation circuitry that receives the first light beam and that applies at least one orbital angular momentum to the plurality of plane waves of the first light beam;
   amplifying circuitry that receives the first light beam after the first light beam passes through the sample and that amplifies a first portion of the first light beam having a predetermined value of the orbital angular momentum associated therewith;
   a detector that receives the first light beam after the first light beam passes through the sample and that determines the concentration of the material within the sample based on a detected value of orbital angular momentum within the amplified portion of the light beam having the predetermined value of the orbital angular momentum associated therewith.

16. The apparatus of claim 15, wherein the orbital angular momentum generation circuitry comprises a fixed orbital angular momentum generation circuitry that applies a fixed orbital angular momentum to the first light beam.

17. The apparatus of claim 15, wherein the orbital angular momentum generation circuitry comprises a tunable orbital angular momentum generation circuitry that applies a selected orbital angular momentum to the first light beam responsive to at least one tuning parameter provided to the tunable orbital angular momentum generation circuitry.

18. The apparatus of claim 15, wherein the orbital angular momentum generation circuitry comprises:
   at least one pi/2 mode converter for converting the first light beam from Hermite-Guassian modes to Laguerre-Gaussian modes;
   a converter for converting the first light beam in the Laguerre-Gaussian modes to reversed Laguerre-Gaussian modes.

19. The apparatus of claim 15, wherein differing values of the concentration indicate different concentrations of the material within the sample.

20. The apparatus of claim 15, wherein the orbital angular momentum generation circuitry further includes a hologram for applying the at least one orbital angular momentum to the plurality of plane waves of the first light beam.

21. The apparatus of claim 15 further comprising a processor that determines the concentration of the material within the sample responsive to the detected value of the orbital angular momentum.

22. The apparatus of claim 20, wherein the hologram comprises a pair of superimposed holograms comprising a composite vortex grid.

23. The apparatus of claim 21 further including a user interface associated with the processor comprising:
   a set of computer instructions that configures the processor to determine the concentration of the material within the sample responsive to the detected value of the orbital angular momentum;
   a database that stores concentration data from concentrations determined by the processor.

24. The apparatus of claim 23, wherein the user interface further includes a wireless interface that communicates the concentration data to a remote location.

25. A method for measuring a concentration of a material within a sample, comprising:
   generating a first signal having at least one orbital angular momentum applied thereto;
   applying the first signal to the sample;
   receiving the first signal after the first signal passes through the sample;
   detecting a value of the orbital angular momentum within the received first signal; and
   determining the concentration of the material within the sample based on the detected value of orbital angular momentum with the first signal received from the sample.

26. The method of claim 25 further including:
   receiving the first signal after the first signal passes through the sample; and
   amplifying a first portion of the signal having the detected value of the orbital angular momentum associated therewith.

27. The method of claim 25 further including storing concentration data from concentrations that are determined.

28. The method of claim 25, wherein the step of generating further comprises:
   emitting the first signal comprising a plurality of plane waves;
   receiving the first signal; and
   applying the at least one orbital angular momentum to the plane waves of the first signal.

29. The method of claim 28, wherein the step of applying further comprises applying a fixed orbital angular momentum to the first signal.

30. The method of claim 28, wherein the step of applying further comprises applying a selected orbital angular momentum to the first signal responsive to at least one tuning parameter provided to the tunable orbital angular momentum generation circuitry.

* * * * *